United States Patent [19]
Bisagni et al.

[11] Patent Number: 6,015,820
[45] Date of Patent: Jan. 18, 2000

[54] 4-ARYL-THIO-PYRIDIN-2(1H)-ONES, MEDICINES CONTAINING THEM AND THEIR USES IN THE TREATMENT OF ILLNESSES LINKED TO HIV

[75] Inventors: Emile Bisagni; Valérie Dolle, both of Orsay; Chi Hung Nguyen, Massy; Michel Legraverend, Antony; Anne-Marie Aubertin; André Kirn, both of Strasbourg; Marie-Line Andreola, La Brede; Laura Tarrago-Litvak, Pessac; Michel Ventura, Villenave D'Ornon, all of France

[73] Assignee: Centre National de la Recherche Scientifique (CNRS), Paris Cedex, France

[21] Appl. No.: 09/000,142
[22] PCT Filed: Jul. 30, 1996
[86] PCT No.: PCT/FR96/01204
§ 371 Date: Apr. 15, 1998
§ 102(e) Date: Apr. 15, 1998
[87] PCT Pub. No.: WO97/05113
PCT Pub. Date: Feb. 13, 1997

[30] Foreign Application Priority Data

Jul. 31, 1995 [FR] France .................................. 95/09323

[51] Int. Cl.[7] .................. A61K 31/44; C07D 213/70; C07D 213/73; C07D 213/75; C07D 215/38

[52] U.S. Cl. .................. 514/348; 514/309; 546/297; 546/298; 546/142

[58] Field of Search .................. 546/297, 298, 546/142; 514/348, 309

[56] References Cited

PUBLICATIONS

V. Dolle et al., Journal of Medicinal Chemistry, vol. 38, pp. 4679–4686 (1995).

*Primary Examiner*—Alan L. Rotman
*Attorney, Agent, or Firm*—Oblon, Spivak, McClelland, Maier & Neustadt, P.C.

[57] ABSTRACT

Compounds of formula (3) in which:
$R_1$ and $R_2$ independently represent an atom of hydrogen, an aliphatic group or an alkyloxyalkyl group in which the alkyl chains are from $C_1$ to $C_4$ or together form an aromatic ring;
$R_3$ represents:
an atom of hydrogen, or
an $NHR_5$ group in which $R_5$ represents an atom of hydrogen or a $COR_6$ group in which $R_6$ is an aliphatic or aromatic group, or
an $NO_2$ group or
a $COOR_7$ group in which $R_7$ is an aliphatic group,
$R_4$ represents a phenyl or heterocyclic group.

These compounds can be used in the treatment of illnesses linked to the HIV virus.

16 Claims, 11 Drawing Sheets

(1a)(HEPT) : R' = CH₃ AND R" = OH
(1b)(E-EPU) : R' = CH₂CH₃ AND R" = H (2a) : X = CH₂ AND R''' = H (L-696,229)
(2b) : X = NH 8a (8c) ⟶

11 (11g)

11a : R$_5$ = CHO, R$_4$ = CH$_3$, R$_2$ = H
11b : R$_5$ = COCH$_3$, R$_4$ = CH$_3$, R$_2$ = H
11c : R$_5$ = COCH$_2$CH$_3$, R$_4$ = CH$_3$, R$_2$ = H
11d : R$_5$ = CO(CH$_2$)$_5$CH$_3$, R$_4$ = CH$_3$, R$_2$ = H
11e : R$_5$ = COCH$_2$C$_6$H$_5$, R$_4$ = CH$_3$, R$_2$ = H
11f : R$_5$ = COOCH$_2$CH$_3$, R$_4$ = CH$_3$, R$_2$ = H
11g : R$_5$ = COCH$_3$, R$_4$ = CH$_2$CH$_3$, R$_2$ = CH$_3$

4-ARYL-THIO-PYRIDIN-2(1H)-ONES, MEDICINES CONTAINING THEM AND THEIR USES IN THE TREATMENT OF ILLNESSES LINKED TO HIV

CROSS-REFERENCE

This application is a 5371 of PCT/FR 96/01204 filed Jul. 30, 1996.

The purpose of this invention is 4-aryl-thio-pyridin-2 (1H)-ones and their applications as medicines.

It relates particularly to their uses in the treatment of illnesses linked to the human immunodeficiency virus (HIV).

The derivatives of 1-[(2-hydroxyethoxy)methyl]-6-(phenylthio)thymine (HEPT) and of pyridinones are known for their inhibiting properties for the inverse transcriptase of HIV-1.

HEPT and another derivative of the same family, named E-EPU (5-ethyl-l-ethoxymethyl-6-(phenylthio)-uracil) are represented respectively in FIG. 1 by the formulae (1a) and (1b). Pyridinones having inhibiting properties with respect to the inverse transcriptase are represented in FIG. 2 by the formulae (2a) and (2b).

Other compounds which are inhibitors of the HIV virus inverse transcriptase, including pyridinones, are also described in the patent application EP-0.462.800 (Merck). This application describes, in a general manner, a group of pyridinones that have a particular structure, in which the group $R_4$ in position 4 of the ring is an alkylthio or alkylamino group, and the group in position 3 has to be substituted with an aryl or heterocyclic group, which may be substituted, bonded to the pyridinone nucleus by an X-CHn$R_3$ chain which cannot be NHCO. Nevertheless, only compounds in which $R_4$ is an atom of hydrogen have been synthesised. In any case, this document does not mention that the compounds penetrate the viral particle.

These compounds have the disadvantage of causing the rapid appearance of resistant strains of HIV-1 and their use in a long term course of monotherapy in man in the treatment of illnesses linked to the HIV virus is therefore made difficult.

Another problem posed in the treatment of illnesses linked to the HIV virus is in the blocking of the conversion of genomic RNA into proviral DNA, a step essential to the integration into the eucaryote genome. Recent work clearly shows that this retro-transcription can take place even within the virion, when it is still in its extra-cellular phase. Hence, up to 2% of the viral cells, in the case of seminal liquid, can have their retro-transcription terminated before merging with the target cell. Therefore it is essential that the inhibitors of the inverse transcriptase (IT) can penetrate the virion before it has reached the cell.

Studies by Perelson et al. (1996, Science 271.1582–1586) on viral dynamics show that the average life of a viral particle in blood plasma is of the order of 8 hours or about a quarter of the estimated life of HIV-1 in vivo. The virion, in its extra-cellular phase is therefore a potential target for these inhibitors.

It should be noted that other thiopyridinones not having any anti-HIV-1 activity have been described.

The article by CROISY-DELCEY at al. (1983 J. Med. Chem. vol.26, No. 9, 1329–1333) describes the synthesis of analogues of lucanthone which shows anti-tumour and bactericide activity. The intermediate compounds 7b, 17a and 17b are pyridinones.

The article by RIVALLE et al. ((1980) J. Hétérocycl. Chem., Vol.17, No. 2, 245–248) describes the synthesis of pyridoquinolines, from intermediate compounds, some of which are pyridinones. No activity is mentioned, either for the final compounds or the intermediates.

The article by UPTON ((1986) J. Chem. Soc. Perkin Trans. 1, No. 7, 1225–1229), describes the synthesis of anthracenes by the use of, in particular, hydroxypyridines and not pyridinones.

The applicant has become interested in finding new molecules showing strong inhibiting activity, that is to say, being active at low doses, low cytotoxicity and which penetrate the viral particle.

He has shown that the substituted 4-aryl-thio-pyridin-2 (1H)-ones exhibit strong inhibiting action and low cytotoxicity while penetrating the viral particle.

Hence the object of this invention is compounds of formula (3), represented in FIG. 3, in which:

$R_1$ and $R_2$ independently represent an atom of hydrogen, an aliphatic group or an alkyloxyalkyl group in which the alkyl chains are from $C_1$ to $C_4$ or together form an aromatic ring;

$R_3$ represents:
  an atom of hydrogen, or
  an $NHR_5$ group in which $R_5$ represents an atom of hydrogen or a $COR_6$ group in which $R_6$ is an aliphatic or aromatic group, or
  an $NO_2$ group or
  a $COOR_7$ group in which $R_7$ is an aliphatic group, $R_4$ represents a phenyl, pyrimidine, benzimidazole, benzoxazole, benzothiazole, thiazoline, imidazole or pyridine group optionally substituted by one or more aliphatic groups and/or by one or more hydroxy groups.

Avantageously, $R_1$ and $R_2$ independently represent an atom of hydrogen, an alkyl group from $C_1$ to $C_4$ or an alkyloxymethyl, preferably an ethoxymethyl group. $R_6$ can be an alkyl group from $C_1$ to $C_6$, optionally substituted by a phenyl group or $R_6$ can be a benzyl group.

$R_7$ can be an alkyl group from $C_1$ to $C_6$, in particular an ethyl group.

$R_3$ is then preferably an $NH_2$, $NHCOCH_3$, $NO_2$ or $COOC_2H_5$ group.

$R_4$ is advantageously a phenyl group substituted by alkyl groups, preferably by two methyl groups, and even more preferably a phenyl group substituted in the meta positions by two methyl groups.

The following compounds are particularly advantageous according to this invention:
  5-ethyl-6-methyl-3-nitro-4-(3', 5'-dimethylphenyl)thio-pyridin-2(1H)-one (formula 7c),
  5-ethoxymethyl-3-nitro-4-(3', 5'-dimethylphenyl)thio-pyridin-2(1H)-one (formula 7g),
  3-amino-5-ethyl-6-methyl-4-(3', 5'-dimethylphenyl)thio-pyridin-2(1H)-one (formula 8c)
  3-amino-5-methyl-4-(3', 5'-dimethylphenyl) thio-pyridin-2(1H)-one (formula 8a),
  3-amino-5-ethyl-4-(3', 5'-dimethylphenyl) thio-pyridin-2 (1H)-one (formula 8b),
  3-amino-5-ethoxymethyl-4-(3', 5'-dimethylphenyl)thio-pyridin-2(1H)-one (formula 8g),
  5-ethyl-6-methyl-3-carbethoxy-4-(3', 5'-dimethylphenyl) thio-pyridin-2(1H)-one (formula 15).

This invention also relates to obtaining the compounds according to the invention. Hence the compounds in which $R_3$ represents $NO_2$ (formulae 7 and 9), can be obtained by reacting a chloronitropyridinone of formula (6) with a thio-phenol or a mercapto derivative of an optionally substituted heterocyclic compound of formula $R_4SH$.

The nitropyridinone obtained can be reduced by hydrated stannous chloride or by catalytic hydrogenation for the preparation of compounds in which $R_3$ represents $NH_2$ (formulae 8 and 10).

Hence compounds of formulae 7 and 8, according to the invention, have been synthesised according to the reaction scheme shown in FIG. 4 from the corresponding hydroxypyridin-2(1H)-ones (compounds 4).

Compounds 9a to 9f have been obtained according to the scheme shown in FIG. 5.

As for compounds of formula 4, obtained either as described by Legraverend et al. (Nucleosides and Nucleotides, 1986, 5(2), 125–134) or by reaction of ethyl#2-ethyl-3-aminocrotonate (compound 12) with diethyl malonate so as to obtain intermediate 13 which is itself hydrolysed by hydrochloric acid.

The nitropyridinones (compounds 5) have been prepared by reaction with nitric acid $HNO_3$ and then have been converted into chloronitropyridinones (compounds 6) as described by C. H. Nguyen et al. (Anti-Cancer Drug Design, 1992, 7, 219–233) by reaction of the compounds of formula (5) with a mixture of $POCl_3$/benzyltriethylammonium chloride/$CH_3CN$ heated under reflux.

The condensation of compound (6a) with 3,5-dimethylthiophenol, carried out in the presence of triethylamine in ethanol at ambient temperature, leads to 4-(3', 5'-dimethylphenyl)thio-5-methyl-3-nitropyridin-2(1H)-one (compound 7a). The reduction with dihydrated stannous chloride in ethyl acetate at boiling point leads to the amine of formula 8a.

Compounds 7d, 7e and 8e have been obtained by condensation of the chloronitropyridinone (6a) with thiophenol or m-thiocresol, followed by reduction of the nitro group (in the case of compound 8e).

The aminopyridinone (10) has been obtained by reduction of compound 9d, in the presence of stannous chloride dihydrate and ethyl acetate under reflux.

Compounds in which $R_3$ represents $NHCOR_6$ and $R_4$ represents an optionally substituted phenyl group, can be obtained by reacting a compound of formula $(R_6CO)_2O$ or $R_6COZ$, in which Z is a radical liable to be liberated and to allow the formation of an amide link, with an aminopyridinone.

Hence the amides 11a to 11e and 1g have been synthesised according to the reaction scheme represented in FIG. 6, by modification of the amino group of 3-amino-5-methyl-4-(3', 5'-dimethylphenyl) thio-pyridin-2(1H)-one (formula 8a) or 3-amino-5-ethyl-6-methyl-4-(3', 5'-dimethylphenyl) thio-pyridin-2(1H)-one (formula 8c). The reaction has been carried out in the presence of ethyl formate, acetic anhydride, propionyl chloride, heptanoic anhydride or phenylacetyl chloride.

The 3-N-(ethoxycarbamyl) derivative (compound 11f) has been synthesised under similar conditions, with ethyl chloroformate.

5-ethyl-pyridinone and 5-ethyl-6-methyl-pyridinone have been obtained either by starting from 5-ethyl-4-hydroxy-pyridin-2(1H)-one (compound 4b) or from 5-ethyl-4-hydroxy-6-methyl-pyridin-2(1H)-one (compound 4c). FIG. 7 illustrates the reaction scheme for obtaining compound 4c by a succession of two steps from ethyl#2-ethylaminocrotonate (compound 12). The nitration, monochlorination, the substitution with 3,5-dimethylthiophenol and the reduction of the nitro group are then carried out in accordance with the reaction scheme in FIG. 4, leading to the 3-nitro and 3-amino-pyridinone derivatives 7b and 8b and 7c and 8c respectively. In the same way, the benzopyridinone analogues 7f and 8f have also been obtained by using as the starting compound quinoline 2,4-diol (compound 4f) available commercially.

The compounds in which $R_3$ represents a $COOR_7$ group and $R_4$ represents an optionally substituted phenyl group have been obtained by reacting a 4-chloropyridinone of formula 14 with an optionally substituted thiophenol in accordance with the reaction scheme in FIG. 7. As for the 4-chloropyridinone of formula 14, it can be obtained by the reaction of the hydroxypyridinone of formula 13 in the presence of $POCl_3$ in accordance with the reaction scheme of FIG. 7.

Hence 3-carbethoxy-5-ethyl-4-hydroxy-5-methylpyridin-2(1H)-one (compound 13), obtained as an intermediate product during the preparation of the pyridinone (4c) has been converted successively to the 4-chloropyridinone (compound 14) and to the 4-phenylthiopyridinone (compound 15). The hydrolysis of the 3-carbethoxypyridinone (compound 15) leads, by decarboxylation, to the pyridinone (compound 16) unsubstituted in the 3 position.

The preparation of the compounds according to the invention is not limited to the methods above. They can be obtained by any means known to a man skilled in the art.

A further purpose of this invention is intermediate compounds wed in the synthesis of compounds of formula (3) in which $R_1$ and $R_2$ are independently ethyl or methyl groups and $R_3$ is $NO_2$ or $NH_2$ corresponding to formula (6) in which $R_1$ and $R_2$ have these characteristics.

The invention further relates to intermediate compounds wed in the synthesis of compounds of formula (3) in which $R_1$ and $R_2$ are independently ethyl and methyl groups and $R_3$ is the $CO_2C_2H_5$ group, corresponding to formula (17) shown in FIG. 8 in which $R_1$ and $R_2$ have these characteristics.

In addition, this invention relates to pharmaceutical compositions containing an efficacious quantity of a compound according to the invention as described above in a mixture with compatible excipients.

Another objective is a medicine containing said compounds.

Finally the invention relates to the use of one of these compounds for the manufacture of a medicine for the treatment of illnesses linked to HIV.

Although these compounds can be administered by any known route known to men skilled in the art, they are preferably administered by an oral, parenteral (including subcutaneous, intravenous, intramuscular, intrasternal injections), or rectal route or by inhalation.

The compositions according to this invention are formulated so as to meet the demands of the above-mentioned routes for administration and are, for example in the form of tablets, capsules, sterile injectable solutions, for example, sterile injectable aqueous solutions or oily suspensions, nasal preparations or suppositories.

When they are administered orally, in the form of suspensions, these compositions can be prepared, in accordance with methods known to a man skilled in the art, and may contain microcrystalline cellulose as a filler, alginic acid or sodium alginate as a suspension agent, methylcellulose as an agent to improve the viscosity and flavouring agents.

When they are administered by a nasal route, or by inhalation, these compositions can be in the form of saline solutions, and contain benzyl alcohol or any other suitable preservative, substances intended to improve absorption, so as to improve the bio-availability, fluorocarbons and any other dispersion or solubilising agent known to a man skilled in the art.

The injectable solutions, or suspensions can be formulated using non-toxic diluents or solvents, suitable for the parenteral route, such as mannitol, 1,3-butanediol, water, Ringer's solution or an isotonic sodium chloride solution or any other dispersion, wetting or suspension agent such as sterile oils, in particular the diglycerides or synthetic monoglycerides and fatty acids such as oleic acid.

When they are administered rectally, that is to say in the form of suppositories, these compositions can be prepared by mixing a compound according to the invention with a suitable, non-irritant excipient, such as cocoa butter, synthetic esters of glycerol or polyethylene glycols, which are solid at ordinary temperatures but which liquefy or become dissolved in the rectal cavity so as to release the compound.

The compounds according to this invention can be administered orally in quantities between 1 and 100 mg/kg body weight. However, specific doses and the frequency of treatment vary from patient to patient and can depend on various factors including the activity of the compound used, its metabolic stability, its speed of action as well as the age, weight and general condition of the patient at the time of administration, the rate of excretion, other medicines being used and any other factor inherent to the patient being treated.

The compositions according to this invention are intended to inhibit the inverse transcriptase of the HIV, for the prevention and treatment of infection by HIV, and for the treatment of the pathological consequences of such an infection, such as AIDS. The treatment of AIDS, or the prevention or the treatment of infection by HIV can be defined, without this definition being in any way limitative, as the treatment of a wide range of conditions of infection by HIV, such as AIDS or ARC (Aids Related Complex).

This invention is illustrated without in any way being limited by the examples which follow.

The following Figures illustrate the invention.

Figure 10:
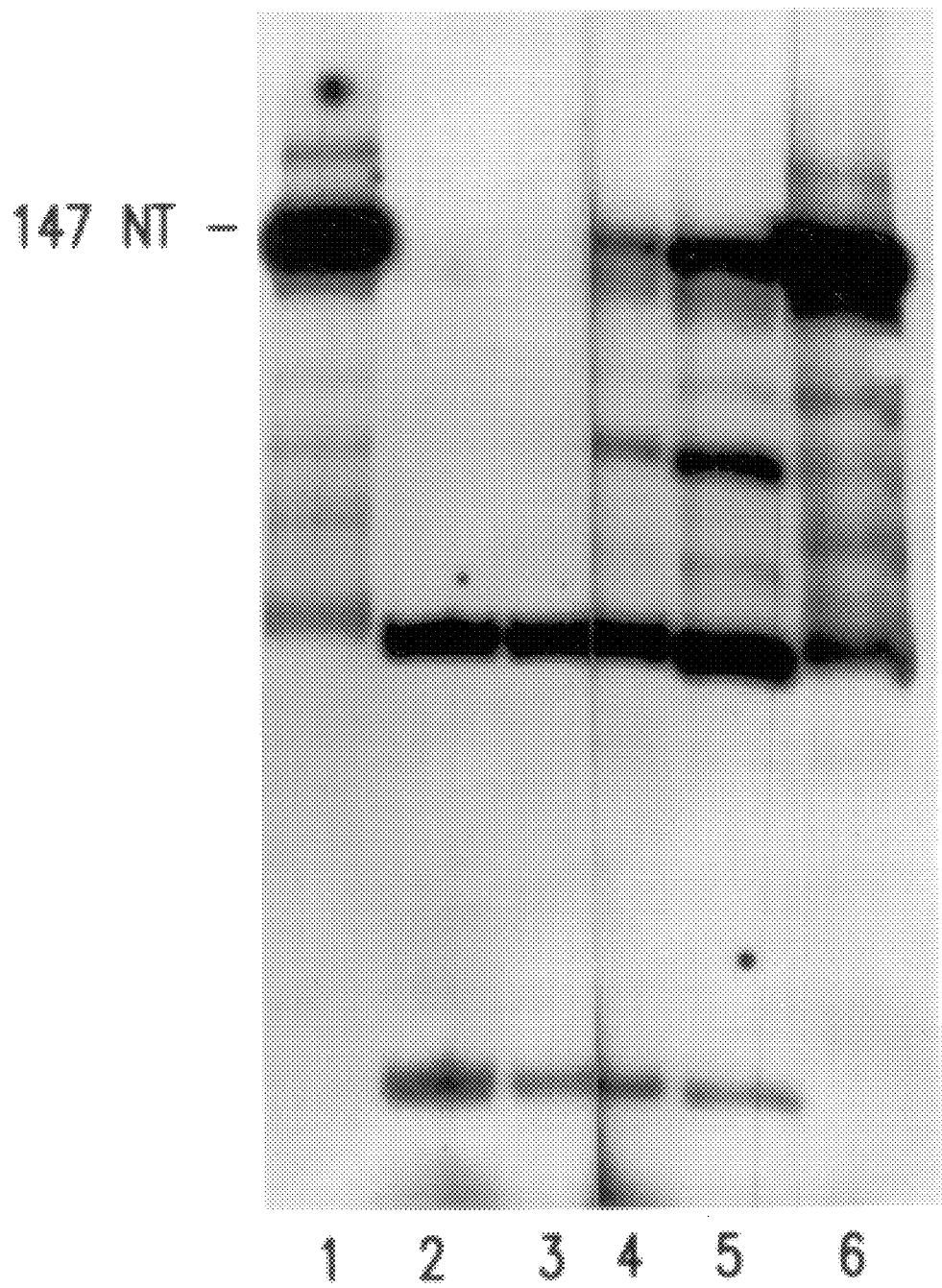

FIG. 10 illustrates the dose effect of compound 7c on the inhibition of the inverse transcriptase of HIV-1. The expected complementary DNA, 147 nucleotides long, is shown to the left of the gel (well 1). Wells 2 to 5 correspond to decreasing concentrations of compound 7c (well 2: 400 nM, well 3: 300 nM: well 4: 100 nM and well 5: 40 nM). Well 6 does not contain any compound 7c.

Figure 11:
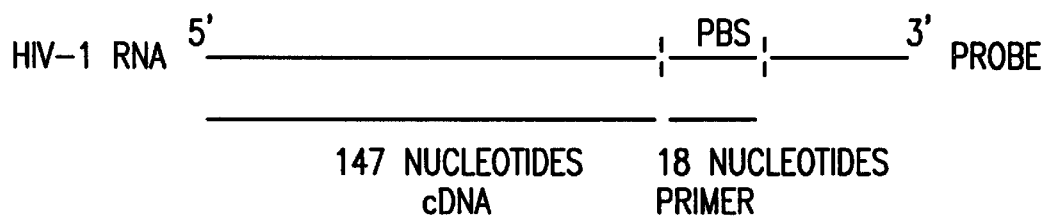

FIG. 11 is a diagram of the probe used to reveal the complementary DNA of FIG. 10.

Figure 12:
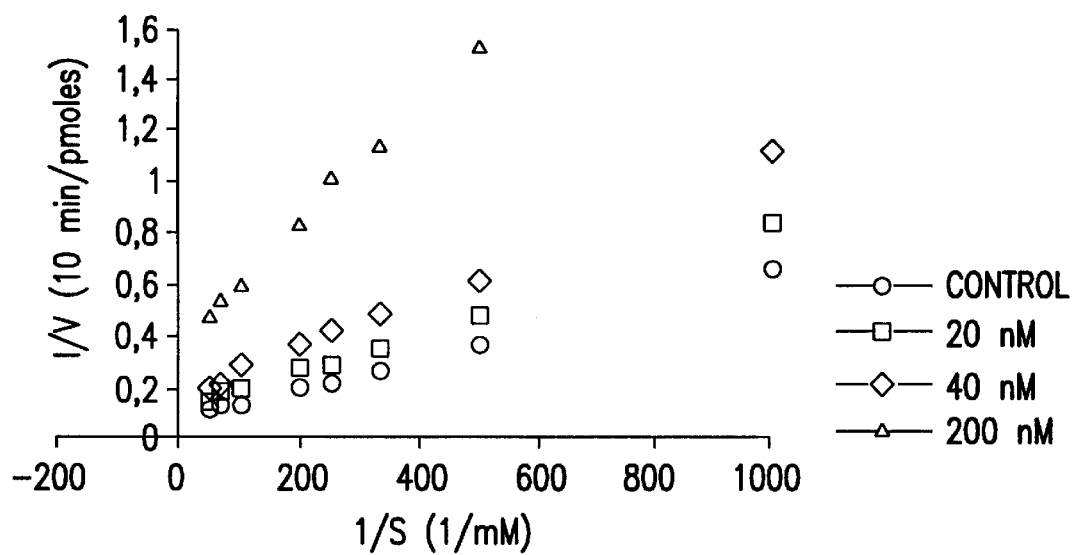

FIG. 12 is a double-reciprocal (Lineweaver-Burk) representation of the inhibition of the inverse transcriptase of HIV-1 by compound 7c with the poly C-oligo dG as a matrix-primer couple and dGPT as substrate.

Figure 1:
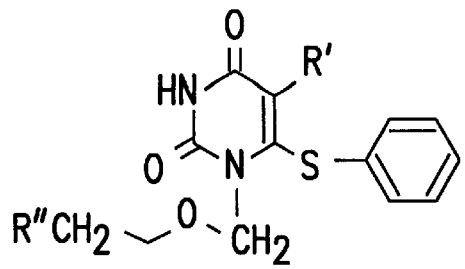
FIGS. 1 to 3 represent respectively the formulae of compounds (1), (2) and (3).
Figure 2:
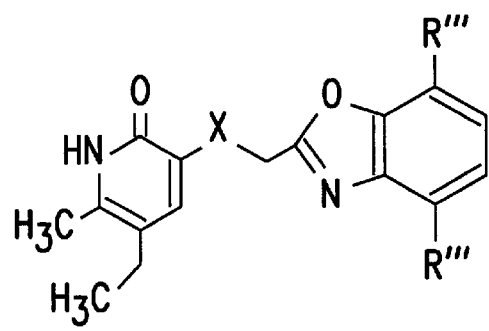
Figure 3:
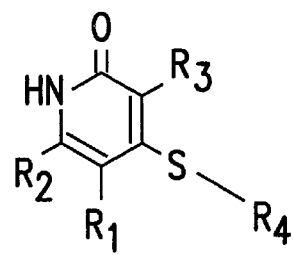
Figure 4:
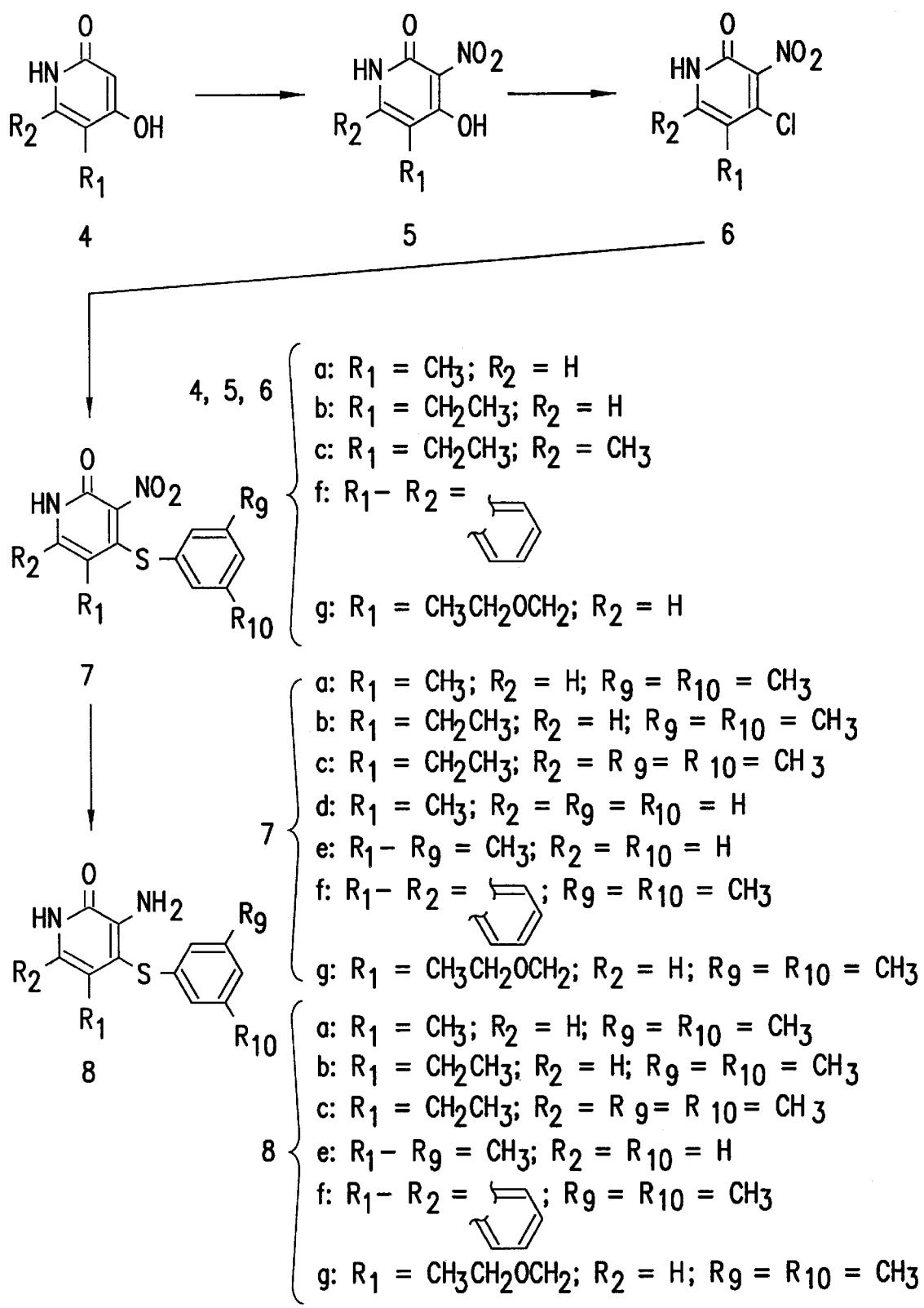
FIGS. 4 to 7 represent the reaction schemes for obtaining the compounds according to the invention.
Figure 5:
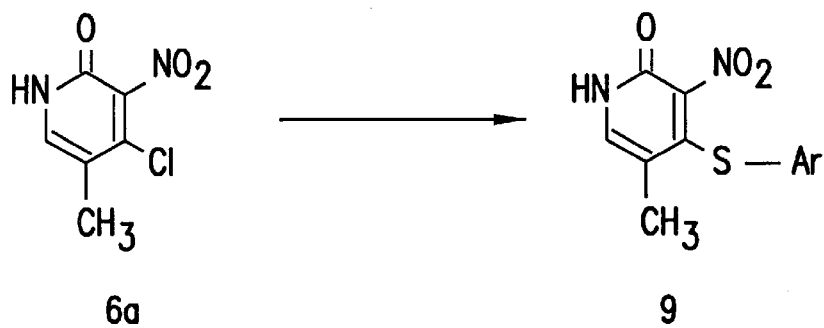
Figure 5:
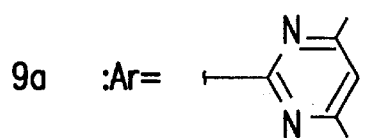
Figure 5:
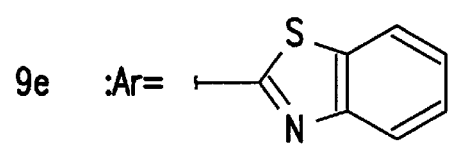
Figure 5:
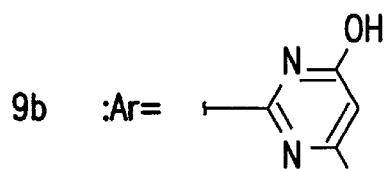
Figure 5:
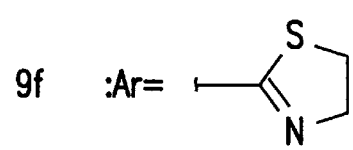
Figure 5:
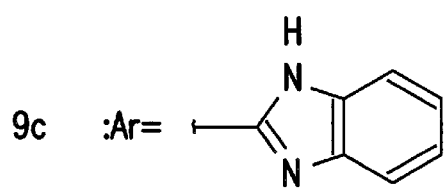
Figure 5:
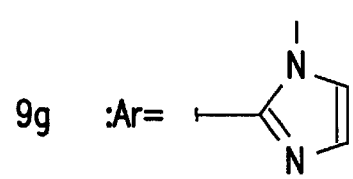
Figure 5:
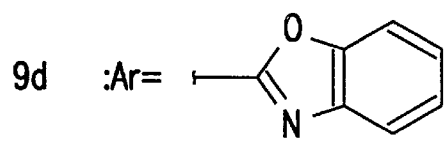
Figure 5:
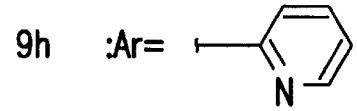
Figure 5:
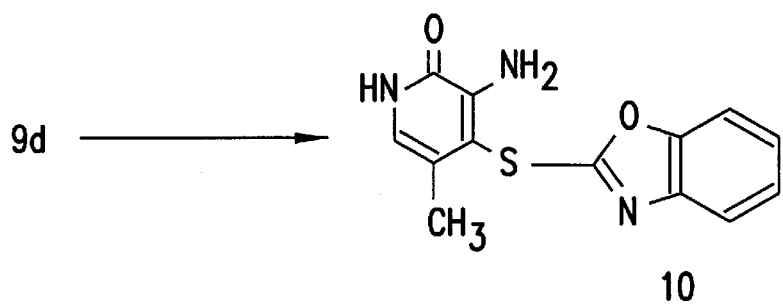
Figure 6:
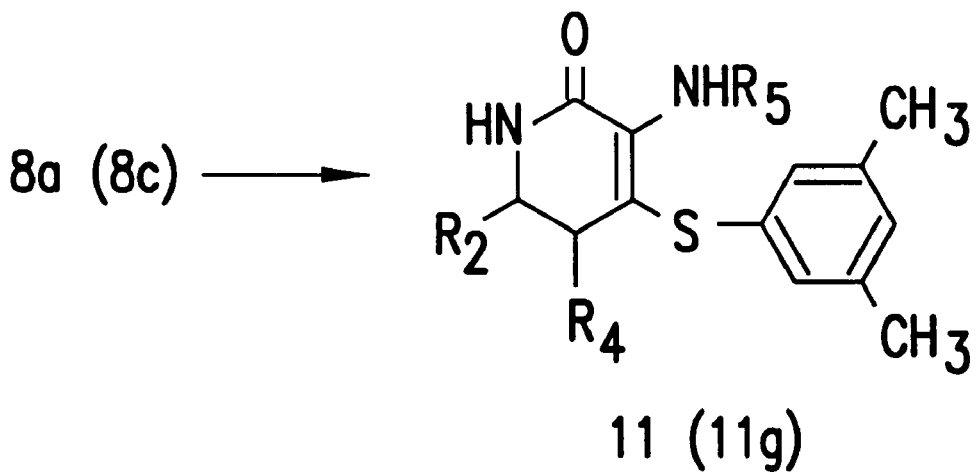
Figure 7:
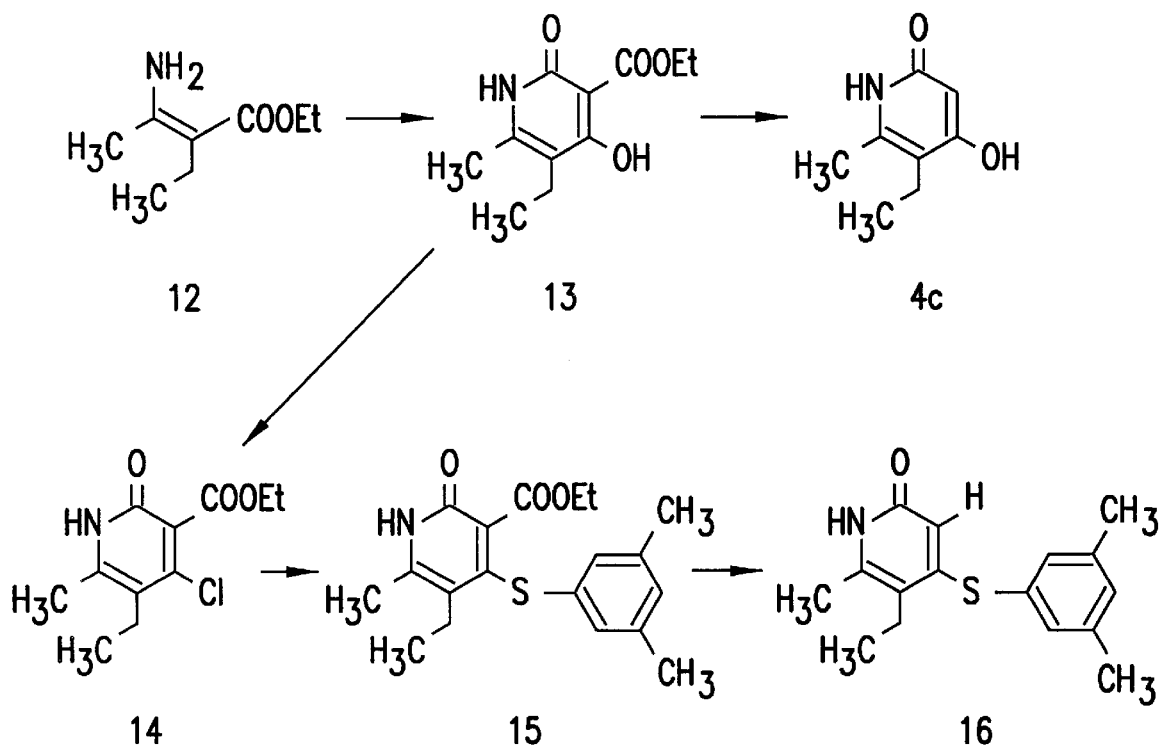
Figure 8:
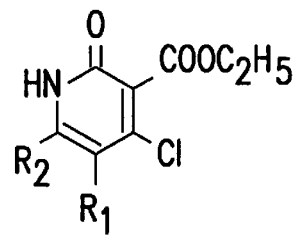
FIG. 8 represents the formula of compound (17).
Figure 9:
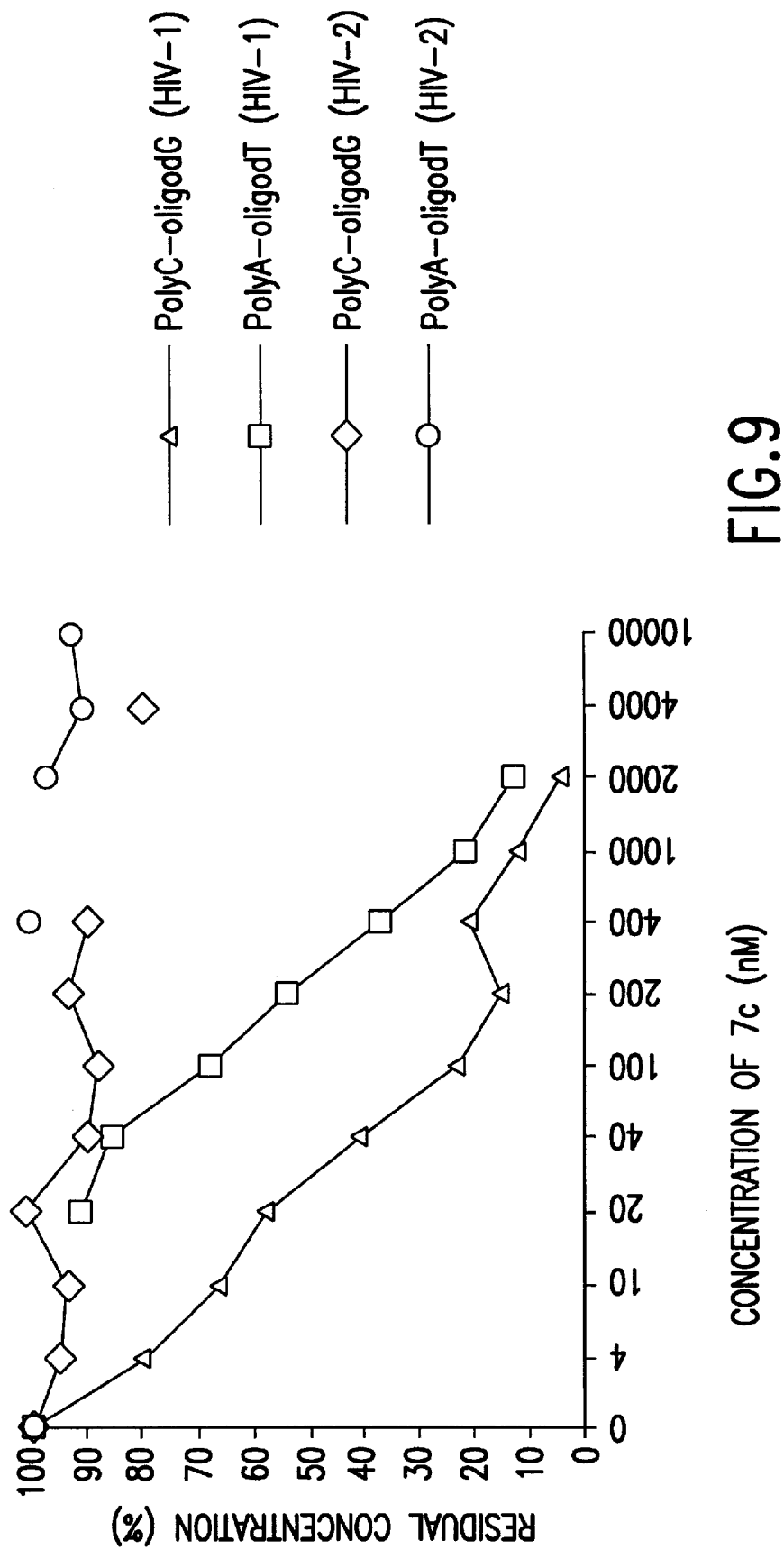
FIG. 9 illustrates the effect of compound 7c on the activity of the inverse transcriptases of the HIV-1 and HIV-2 viruses in the presence of two matrix-primer couples.
Figure 13:
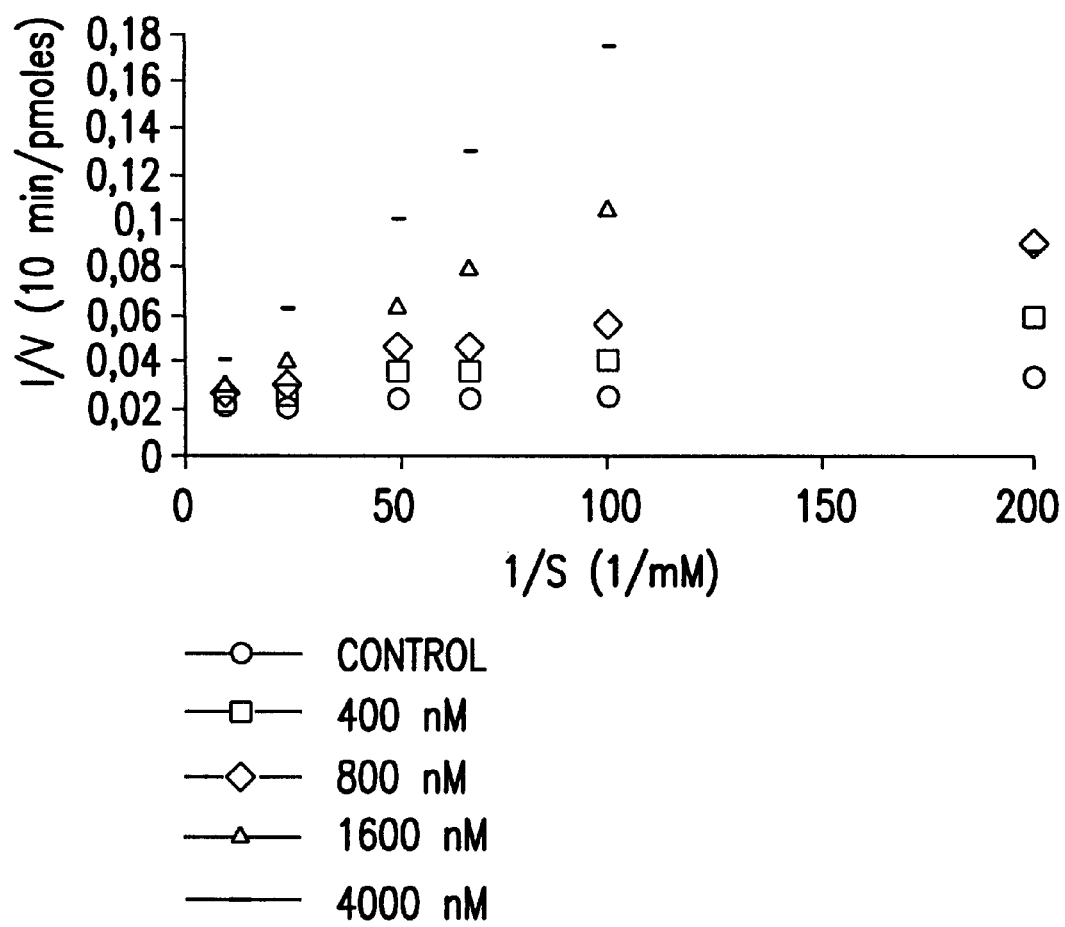

FIG. 13 is a double-reciprocal representation, similar to FIG. 9, in which the poly A-oligo dT is used as a matrix-primer couple and dTTP as substrate.

Figure 14:
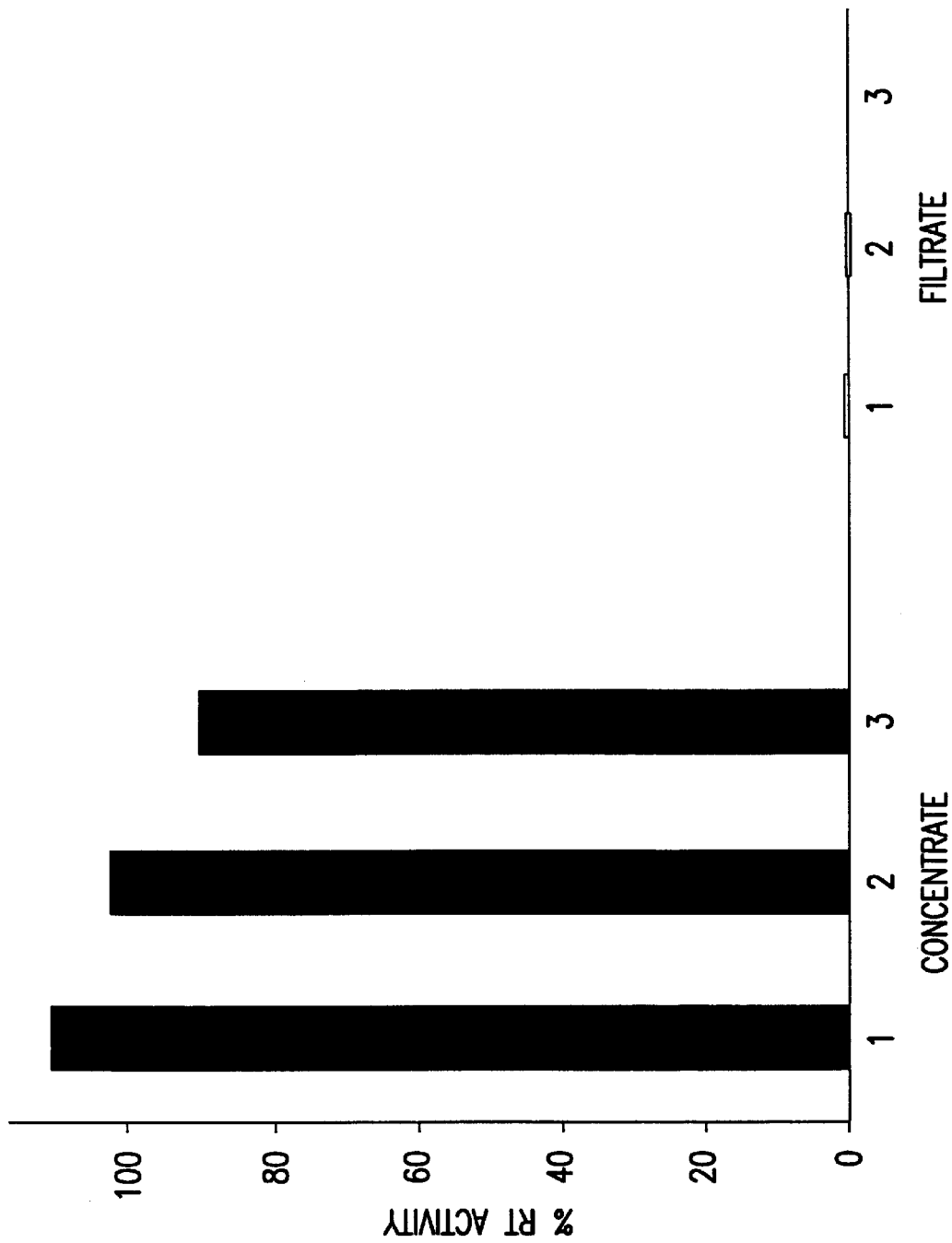
Figure 15:
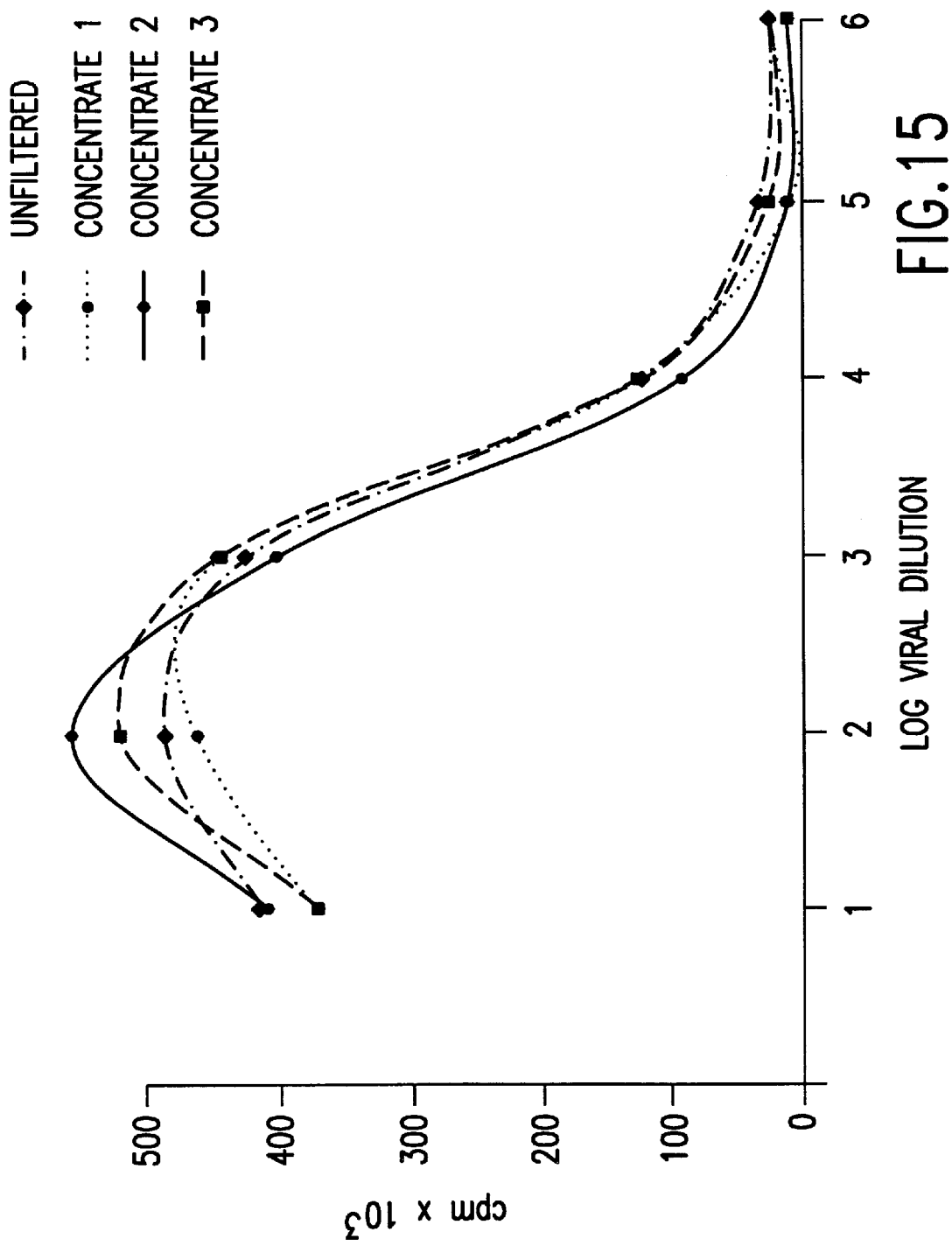

FIG. 14 represents the measurement of the inverse transcriptase activity (IT) after filtration on anapore;

FIG. 15 represents the measurement of the infectiveness after filtration on anapore.

CHARACTERISATION OF THE PRODUCTS

Thin layer chromatography (TLC) was carried out on plates previously covered with silica gel 60F254 (Merck). To detect the compounds, the TLC plates were exposed to UV light. Purification was performed on columns of silica gel (40–60 μm) using medium pressure chromatography. All the melting points were measured on an Electrothermal 9200 apparatus and were not corrected. The NMR-$^1$H spectra were recorded in the solvents given on a Bruker AC 200 apparatus with $CHCl_3$ ($\delta$=7.25 ppm) or DMSO ($\delta$=2.54 ppm) as internal standards (*,#=interchangeable allocations). The elemental analyses (Table 1) were carried out by The Service Central de Microanalyses (The Microanalysis Department) at CNRS, 91190 Gif-sur-Yvette, France.

EXAMPLE 1

Preparation of ethyl#2-ethyl-3-aminocrotonate (compound 12)

Ethyl#2-ethylacetoacetate (150 g, 0.95 mole) and ammonium nitrate (84 g, 1.04 moles) were dissolved in 1.1 l of anhydrous tetrahydrofuran. The mixture was agitated for 5 days with sparging with ammonia. The solvent was evaporated at ambient temperature and 1 l of water was added. The mixture was agitated for 30 minutes. The colourless solid residue was isolated by filtration and recrystallised in hexane to give product 12 (107 g, 72%) in the form of colourless crystals: melting point 61° C.; NMR-$^1$H (CDCl$_3$) $\delta$ 4.11 (2H, q, J=7 hz, OC$\underline{H}_2$CH$_3$), 2.17 (2H, q, J=7 Hz, C$\underline{H}_2$CH$_3$), 1.93 (3H, s, CH$_3$), 1.24 (3H, t, J=7 Hz, OCH$_2$C$\underline{H}_3$), 0.94 (3H, t, J=7 Hz, CH$_2$C$\underline{H}_3$). Anal. C$_8$H$_{15}$NO$_2$ (C,H,N,).

EXAMPLE 2

Preparation of 4-hydroxy-5-ethyl-6-methyl-3-carbethoxy-pyridin-2(1H)-one (compound 13)

Sodium (48.34 g, 2.10 moles, in small pieces in kerosene) was slowly dissolved in 530 ml of ethanol under a nitrogen atmosphere over a period of 3 hours. The mixture was heated under reflux and diethyl malonate (335 ml, 2.20 moles, freshly distilled) was added drop by drop over a period of 30 minutes. Still under reflux, the aminocrotonate (compound 13) (150 g, 0.96 moles) in 200 ml of ethanol was added drop by drop. The mixture was agitated under reflux for 72 hours to give a pale yellow suspension. This suspension was cooled to ambient temperature and the precipitate was isolated by filtration. The solid was dissolved in water, cooled to 0° C. and acidified with an aqueous solution of hydrochloric acid to pH 1. The precipitate was isolated by filtration, washed with water and crystallised in toluene to give product 13 (109.6 g, 51%) in the form of white crystals: melting point 196–197° C.; NMR-$^1$H (DMSO-d$_6$) $\delta$ 11.52 (1H, s, NH*-1), 11.32 (1H, s, OH*), 4.34 (2H, q, J=7 Hz, COOC$\underline{H}_2$CH$_3$), 2.39 (2H, q, J=7.5 Hz, C$\underline{H}_2$CH$_3$), 2.23 (3H, s, CH$_3$-6), 1.31 (3H, t, J=7 Hz, COOCH$_2$C$\underline{H}_3$), 1.02 (3H, t, J=7 Hz, CH$_2$C$\underline{H}_3$). Anal. C$_{11}$H$_{15}$NO$_4$ (C, H, N).

EXAMPLE 3

Preparation of 5-ethyl-4-hydroxy-6-methyl-pyridin-2(1H)-one (compound 4c)

The ester (13) prepared in example 2 (17.2 g, 76.4 mmoles) was dissolved in 1.2 l of an aqueous solution of 1N HCl and the mixture was heated under reflux for 36 hours. After evaporation of the solvent, 100 ml of water was added and the mixture was neutralised with an aqueous solution of ammonia. The precipitate was isolated by filtration and washed with water. Product 4c was obtained (11.2 g, 96%) in the form of a white solid: melting point 360° C.; NMR-$^1$H (DMSO-$d_6$) δ 10.75 (1H, s, NH-1), 5.46 (1H, s, H-3), 2.32 (2H, q, J=7 Hz, $\underline{CH_2}CH_3$), 2.13 (3H, s, $CH_3$-6), 0.99 (3H, t, J=7 Hz, $CH_2\underline{CH_3}$), Anal. $C_8H_{11}N_1O_2$ (C,H,N).

EXAMPLE 4

Preparation of 5-ethyl-4-hydroxy-3-nitropyridin-2 (1H)-one (compound 5b)

A suspension of compound 4b obtained as described by Legraverend et al. (Nucleosides and Nucleotides, 1986, 5(2), 125–134) (5.00 g, 36.0 mmoles) in 40 ml of nitric acid (d=1.33) was agitated for 10 minutes at ambient temperature and at 75° C. for 12 minutes. 150 ml of iced water was added immediately and the yellow precipitate was isolated by filtration and recrystallised in water to give the nitropyridinone 5b (5.4 g, 82%) in the form of yellow crystals: melting point 213–214° C.; NMR-$^1$H (DMSO-$d_6$) δ 11.85 (1H, s, NH-1), 7.39 (1H, s, H-6), 2.42 (2H, q, J=7 Hz, $CH_2$), 1.10 (3H, t, J=7 Hz, $CH_3$), Anal. $C_7H_8N_2O_4 \cdot 0.25H_2O$ (C,H,N).

EXAMPLE 5

Preparation of 5-ethyl-4-hydroxy-6-methyl-3-nitropyridin-2(1H)-one (compound 5c)

As described for compound 5b in example 4, a suspension of compound 4c (4.00 g, 26.0 mmoles) in 32 ml of nitric acid (d=1.33) was agitated for 10 minutes at ambient temperature and at 80° C. for 10 minutes. 80 ml of iced water was added immediately and the precipitate was isolated by filtration and was recrystallised in water to give the nitropyridinone 5c (4.4 g, 85%) in the form of yellow crystals: melting point 255–256° C.; NMR-$^1$H (DMSO-$d_6$) δ 11.90(IH,s,NH-1), 2.47 (2H, q, J=7 Hz, $\underline{CH_2}CH_3$), 2.27 (3H, s, $CH_3$-6), 1.03 (3H, t, J=7 Hz, $CH_2\underline{CH_3}$), Anal. $C_8H_{10}N_2O_4$ (C,H,N).

EXAMPLE 6

Preparation of 4-hydroxy-3-nitroquinolin-2(1H)-one (compound 5f)

As described for compound 5b in example 4, a suspension of compound 4f (9.00 g, 55.8 mmoles) in 70 ml of nitric acid (d=1.33) was agitated for 15 minutes at ambient temperature and at 80° C. for 15 minutes. 250 ml of iced water was added immediately and the yellow precipitate was isolated by filtration, washed with water and dried over $P_2O_5$ under vacuum to give the nitropyridinone 5f (11.3 g, 98%) in the form of a yellow solid: melting point 250° C.; NMR-$^1$H (DMSO-$d_6$) δ 11.85 (1H, s, NH-1), 8.06 (1H, d, J=8 Hz, H-8), 7.68 (1H, td, $J_1$=8 Hz, $J_2$=1 Hz, H-5), 7.37–7.26 (2H, m, H-6 and 7). Anal. $C_9H_6N_2O_4$ (C,H,N).

EXAMPLE 7

Preparation of 4-chloro-5-ethyl-3-nitropyridin-2 (1H)-one (compound 6b)

Phosphorus oxychloride (6.7 ml, 39.1 mmoles) was added to a solution of compound 5b (3.00 g, 16.3 mmoles) and benzyltriethylammonium chloride (14.90 g, 65.2 mmoles) in acetonitrile (60 ml). The mixture obtained was agitated at 40° C. for 30 minutes and heated under reflux for 1 hour. After evaporation of the solvent, 60 ml of water was added and the mixture agitated at ambient temperature for 3 hours. The yellow precipitate was collected, washed with cyclohexane (3×6 ml) and dried to give compound 6b (2.4 g, 74%) in the form of pale yellow crystals: NMR-$^1$H (DMSO-$d_6$) δ 13.19 (1H, s, NH-1), 7.73 (1H, s, H-6), 2.56 (2H, q, L=7.5 Hz, $CH_2CH_3$), 1.16 (3H, t, J=7.5 Hz, $CH_2CH_3$ ).

EXAMPLE 8

Preparation of 4-chloro-5-ethyl-6-methyl-3-nitropyridin-2(1H)-one (compound 6c)

As described for compound 6b in example 7, phosphorus oxychloride (8.3 ml, 88.8 mmoles) was added to a solution of compound 5c (4.00 g, 20.2 mmoles) and benzyltriethylammonium chloride (18.40 g, 80.8 mmoles) in acetonitrile (80 ml). The mixture obtained was agitated at 40° C. for 30 minutes and heated under reflux for 1 hour. After evaporation of the solvent, 150 ml of water was added and the mixture agitated at ambient temperature for 48 hours. The brown precipitate was collected, washed with cyclohexane (3×10 ml) and recrystallised in ethanol to give compound 6c (1.5 g, 34%) in the form of pale yellow crystals: NMR-$^1$H (DMSO-$d_6$) δ 12.98 (1H, s, NH-1), 2.58 (2H, q, L=7.5 Hz, $\underline{CH_2}CH_3$), 2.38 (3H, s, $\underline{CH_3}$-6), 1.08 (3H, t, J=7.5 Hz, $CH_2\underline{CH_3}$ ).

EXAMPLE 9

Preparation of 4-chloro-3-nitro-2-guinoline-2(1H)-one (compound 6f)

As described for compound 6b in example 7, phosphorus oxychloride (4.0 ml, 46.6 mmoles) was added to a solution of compound 5f (4.00 g, 19.4 mmoles) and benzyltriethylammonium chloride (17.68 g, 77.6 mmoles) in acetonitrile (80 ml). The mixture obtained was agitated at 45° C. for 30 minutes under an atmosphere of nitrogen and heated under reflux for 20 minutes. After evaporation of the solvent, 120 ml of iced water was added. The mixture was neutralised with 12 ml of a dilute aqueous ammonia solution (14%) at 0° C. and agitated at this temperature for 1 hour. The yellow precipitate was collected, and agitated with 120 ml of hexane for 1 hour. After filtration compound 6f (2.9 g, 67%) was dried over $P_2O_5$ under vacuum to give a yellow solid : NMR-$^1$H (DMSO-$d_6$) δ 12.10 (1H, s, NH-1), 8.04 (1H, d, J=8 Hz, H-8), 7.84 (1H, t, J=8 Hz, H-5), 7.54–7.43 (2H, m, H-6 and 7).

EXAMPLE 10

Preparation of 5-methyl-3-nitro-4-(3', 5'-dimethylphenyl)thiopyridin-2(1H)-one (compound 7a)

A mixture of compound 6a obtained according to Nguyen et al. (1992, previously quoted) (1.88 g, 10.0 mmoles) in 20 ml of ethanol and 2 ml of triethylamine was agitated until homogeneous. 3,5-dimethylthiophenol (1.39 g, 10.1 mmoles) was added drop by drop. After 1 hour of agitation at ambient temperature, the precipitate was isolated by filtration and washed with cyclohexane (20 ml). The product 7a was obtained (2.66 g, 92%) in the form of a yellow solid: melting point 235° C.; NMR-$^1$H (DMSO-$d_6$) δ 12.27 (1H, s, NH-1), 7.63 (1H, s, H-6), 7.01 (1H, s, H-4'), 6.96 (2H, s, H-2' and 6') 2.27 (6H, s, $CH_3$-3' and 5'), 1.89 (3H, s, CH3-5). Anal. $C_{14}H_{14}N_2O_3S \cdot 0.25H_2O$ (C, H, N, S).

EXAMPLE 11

Preparation of 5-ethyl-3-nitro-4-(3', 5'-dimethylphenyl)thio-pyridin-2(1H)-one (compound 7b)

As described for compound 7a in example 10, a mixture of compound 6b (2.42 g, 11.9 mmoles) in 20 ml of ethanol and 2 ml of triethylamine was agitated until homogeneous. 3,5-dimethylthiophenol (1.64 ml, 12.1 mmoles) was added drop by drop. After 4 hours of agitation at ambient temperature, the precipitate was isolated by filtration and recrystallised in ethanol (15 ml). The product 7b was obtained (1.94 g, 53%) in the form of yellow crystals: melting point 197° C.; NMR-$^1$H (DMSO-d$_6$) δ 12.29 (1H, s, NH-1), 7.59 (1H, s, H-6), 7.00 (1H, s, H-4'), 6.94 (2H, s, H-2' and 6'), 2.36 (2H, q, J=8 Hz C$\underline{H}_2$CH$_3$ ), 2.26 (6H, s, CH$_3$-3' and 5'), 1.03 (3H, t, J=7 Hz, CH$_2$C$\underline{H}_3$ ). Anal. C$_{15}$H$_{16}$N$_2$O$_3$S (C, H, N, S).

EXAMPLE 12

Preparation of 5-ethyl-6-methyl-3-nitro-4-(3', 5'-dimethylphenyl)thio-pyridin-2(1H)-one (compound 7c)

As described for compound 7a in example 10, a mixture of compound 6c (0.90 g, 4.1 mmoles) in 16 ml of ethanol and 9 ml of triethylamine was agitated until homogeneous. 3,5-dimethylthiophenol (0.57 ml, 4.2 mmoles) was added drop by drop. After 3 hours of agitation at ambient temperature, the precipitate was isolated by filtration and crystallised in ethanol (50 ml). The product 7c was obtained (1.07 g, 81%) in the form of yellow crystals: melting point 236–237° C.; NMR-$^1$H (DMSO-d$_6$) δ 12.28 (1H, s, NH-1), 6.98 (1H, s, H-4'), 6.94 (2H, s, H-2' and 6') 2.26 (6H, s, CH3-3' and 5'), 2.12 (3H, s, CH3-6), 0.87 (3H, t, J=7 Hz, CH$_2$C$\underline{H}_3$ ), the signal from CH$_2$C$\underline{H}_3$ and the signal from the DMSO overlap each other. Anal. C$_{16}$H$_{18}$N$_2$O$_3$S (C, H, N, S).

EXAMPLE 13

Preparation of 5-methyl-3-nitro-4-phenylthio-pyridin-2(1H)-one (compound 7d)

As described for compound 7a in example 10, a mixture of compound 6a (0.20 g, 1.1 mmoles) in 2 ml of ethanol and 0.2 ml of triethylamine was agitated until homogeneous. Thiophenol (0.12 g, 1.1 mmoles) was added. After 15 hours of agitation at ambient temperature, the yellow precipitate was isolated by filtration and washed with ethanol to give the product 7d (0.13 g, 47%) in the form of a yellow solid: melting point 214–216° C.; NMR-$^1$H (DMSO-d$_6$) δ 12.86 (1H, s, NH-1), 7.65 (1H, s, H-6), 7.45–7.36 (5H, m, H-2', 3', 4', 5' and 6'), 1.89 (3H, s, CH$_3$-5). Anal. C$_{12}$H$_{10}$N$_2$O$_3$S. 0.125H$_2$O (C, H, N, S).

EXAMPLE 14

Preparation of 5-methyl-3-nitro-4-(3'-methylphenyl) thio-pyridin-2(1H)-one (compound 7e)

As described for compound 7a in example 10, a mixture of compound 6a (0.50 g, 2.6 mmoles) in 10 ml of ethanol and 0.3 ml of triethylamine was agitated until homogeneous. m-thiocresol (0.35 g, 2.8 mmoles) in 5 ml of ethanol was added drop by drop. After 15 hours of agitation at ambient temperature, the solvent was evaporated and 15 ml of water added. The suspension was agitated for 2 hours at ambient temperature. The yellow precipitate was isolated by filtration, washed with 6×2 ml of water, dried and recrystallised in ethanol to give product 7e (0.52 g, 71%) in the form of yellow needles: melting point 222–223° C.; NMR-$^1$H (DMSO-d$_6$) δ 12.85 (1H, s, NH-1), 7.64 (1H, s, H-6), 7.27 (1H, t, J=8 Hz, H-5'), 7.20–7.14 (3H, m, H-2', 4' and 6'), 2.31 (3H, s, CH$_3$-3'), 1.89 (3H, s, CH$_3$-5). Anal. C$_{13}$H$_{12}$N$_2$O$_3$S. 0.25H$_2$O (C, H, N, S).

EXAMPLE 15

Preparation of 3-nitro-4-(3', 5'-dimethylphenyl)-thiopuinoline-2(1H)-one (compound 7f)

As described for compound 7a in example 10, a mixture of compound 6f (1.40 g, 6.2 mmoles) in 50 ml of ethanol and 1.3 ml of triethylamine was agitated until homogeneous. 3', 5'-dimethylthiophenol (0.86 ml, 6.3 mmoles) in 30 ml of ethanol was added drop by drop over a period of 15 minutes. The receptacle was fitted with a trap containing CaCl$_2$. After 2 hours 30 minutes, with agitation at 50° C., the solvent was evaporated and 100 ml of water added. The mixture was neutralised with a dilute aqueous solution of ammonia and agitated at ambient temperature for 1 hour. The brown precipitate was isolated by filtration, washed with hexane and crystallised in ethanol (200 ml). The product 7f was obtained (1.19 g, 59%) in the form of orange-yellow crystals: melting point 294° C.; NMR-$^1$H (DMSO-d$_6$) δ 12.89 (1H, broad, NH-1), 7.96 (1H, dd, J$_1$=8 Hz, J$_2$=1 Hz, H-8), 7.70 (1H, td, J$_1$=8 Hz, J$_2$=1 Hz, H-5), 7.48 (1H, d, J=8 Hz, H-6*), 7.31 (1H, td, J$_1$=8 Hz, J$_2$=1 Hz, H-7*), 7.05 (2H, s, H-2' and 6'), 6.98 (1H, s, H-4'), 2.23 (6H, s, CH$_3$-3' and 5'). Anal. C$_{17}$H$_{14}$N$_2$O$_3$S (C, H, N, S).

EXAMPLE 16

Preparation of 5-ethoxymethyl-3-nitro-4-(3', 5'-dimethylphenyl)thio-pyridin-2(1H)-one (compound 7p)

As described for compound 7a in example 10, a mixture of compound 6g obtained according to C. H. Nguyen et al. (1992, previously quoted) (0.15 g, 0.6 mmoles) in 5 ml of ethanol and 0.1 ml of triethylamine was agitated until homogeneous. 3',5'-dimethylthiophenol (0.09 g, 0.6 mmoles) in 3 ml of ethanol was added drop by drop. After 2 hours with agitation at ambient temperature, the solvent was evaporated and 10 ml of water was added. The mixture was made basic by the addition of 0.5 ml of a dilute aqueous ammonia solution (14%) and the suspension was agitated at ambient temperature for 2 hours. The yellow precipitate was isolated by filtration, washed with water and hexane and dried to give the product 7g (0.16 g, 74%) in the form of a cream coloured powder: melting point 143–144° C.; NMR-$^1$H (DMSO-d$_6$) δ 12.25 (1H, S, NH-1), 7.75 (1H, S, H-6), 7.01 (1H, S, H-4'), 6.98 (2H, S, H-2' and 6'), 4.23 (2H, S, OCH$_2$-5), 3.37 (2H, q, J=7H$_2$, CH$_3$C$\underline{H}_2$O), 2.26 (6H, S, CH$_3$-3' and 5'), 1.08 (3H, t, J=7H$_2$, CH$_3$CH$_2$O). Anal. C$_{16}$H$_{18}$N$_2$O$_4$S (C, H, N, S).

EXAMPLE 17

Preparation of 3-amino-5-methyl-4-(3', 5'-dimethylphenyl)-thio-pyridin-2(1H)-one (compound 8a)

Stannous chloride dihydrate (9.75 g, 43.0 mmoles) was added to a suspension of compound 7a (2.50 g, 8.6 mmoles) in ethyl acetate (150 ml). The mixture was heated under reflux under an argon atmosphere for 1 hour. After cooling to 0° C., iced water was added (110 ml) and a saturated solution of sodium carbonate until a basic pH was obtained. The precipitate was removed by filtration. The filtered phases were separated and the aqueous phase was extracted with ethyl acetate. The collected organic phases were washed with a saturated aqueous sodium chloride solution (3×120 ml), dried over magnesium sulphate and evaporated. The residue was purified by column chromatography with a mixture of dichloromethane and ethanol (9:1) as eluant to give the product 8a (2.02 g, 87%) in the form of a pale yellow solid: melting point 208° C.; NMR-$^1$H (DMSO-$d_6$) δ 11.46 (1H, s, NH-1), 6.82 (1H, s, H-4'), 6.72 (2H, s, H-2' and 6'), 6.62 (1H, s, H-6), 5.46 (2H, s, NH$_2$-3), 2.22 (6H, s, CH$_3$-3' and 5'), 1.97 (3H, s, CH$_3$-5). Anal. C$_{14}$H$_{16}$N$_2$OS (C, H, H, S).

EXAMPLE 18

Preparation of 3-amino-5-ethyl-4-(3', 5'-dimethylphenyl)thio-pyridin-2(1H)-one (compound 8b)

As described for compound 8a in example 17, stannous chloride dihydrate (6.67 g, 29.6 mmoles) was added to a suspension of compound 7b (1.80 g, 5.9 mmoles) in ethyl acetate (100 ml). The mixture was heated at 70° C. under an argon atmosphere for 1 hour. After cooling to 0° C., the solution was neutralised with a saturated solution of sodium carbonate (90 ml). The precipitate was removed by filtration. The filtered phases were separated and the aqueous phase was extracted with dichloromethane. The collected organic phases were washed with a saturated aqueous sodium chloride solution (3×120 ml), dried over magnesium sulphate and evaporated. The residue was purified by column chromatography with a mixture of dichloromethane and ethanol (9:1) as eluant to give the product 8b (1.04 g, 64%) in the form of a pale beige solid: melting point 208–209° C.; NMR-$^1$H (DMSO-$d_6$) δ 11.51 (1H, s, NH-1), 6.81 (1H, s, H-4'), 6.68 (2H, s, H-2' and 6'), 6.56 (1H, s, H-6), 5.43 (2H, s, NH$_2$-3), 2.40 (2H, q, J=7.5 Hz, $\underline{CH}_2$CH$_3$), 2.21 (6H, s, CH$_3$-3' and 5'), 1.04 (3H, t, J=7 Hz, CH$_2$$\underline{CH}$3). Anal. C$_{15}$H$_{18}$N$_2$OS 0.25H$_2$O (C, H, N, S).

EXAMPLE 19

Preparation of 3-amino-5-ethyl-6-methyl-4-(3', 5'-dimethylphenyl)thio-pyridin-2(1H)-one (compound 8c)

As described for compound 8a in example 17, stannous chloride dihydrate (3.11 g, 13.2 mmoles) was added to a suspension of compound 7c (1.00 g, 3.1 mmoles) in ethyl acetate (50 ml). The mixture was heated at 70° C. under an argon atmosphere for 1 hour. After cooling to 0° C., the solution was neutralised with a saturated solution of sodium carbonate (60 ml). The precipitate was removed by filtration. The filtered phases were separated and the aqueous phase was extracted with dichloromethane. The collected organic phases were washed with a saturated aqueous sodium chloride solution (3×120 ml), dried over magnesium sulphate and evaporated. The residue was purified by column chromatography with a mixture of dichloromethane and ethanol (95:5) as eluant and at the end, ethyl acetate to give the product 8c (0.80 g, 88%) in the form of a pale yellow solid: melting point 188–189° C.; NMR-$^1$H (DMSO-$d_6$) δ 11.52 (1H, s, NH-1), 6.80 (1H, s, H-4'), 6.70 (2H, s, H-2' and 6'), 5.17 (2H, s, NH$_2$-3), 2.21 (6H, s, CH$_3$-3' and 5'), 2.12 (3H, s, CH$_3$-6), 0.93 (3H, t, J=7 Hz, CH$_2$$\underline{CH}_3$), the signal from CH$_2$$\underline{CH}_3$ and the signal from the DMSO overlap one another. Anal. C$_{16}$H$_{20}$N$_2$OS (C, H, N, S).

EXAMPLE 20

Preparation of 3-amino-5-methyl-4-(3', 5'-dimethylphenyl)thio-pyridin-2(1H)-one (compound 8e)

As described for compound 8a in example 17, stannous chloride dihydrate (1.12 g, 5.0 mmoles) was added to a suspension of compound 7e (0.36 g, 1.3 mmoles) in ethyl acetate (25 ml). The mixture was heated at 80° C. under an argon atmosphere for 20 hours. After cooling to ambient temperature, the solution was neutralised with a saturated solution of sodium carbonate (30 ml). The yellow colour of the mixture became red. After agitation for 15 minutes, the precipitate was removed by filtration on celite. The filtered phases were separated and the aqueous phase was extracted with dichloromethane. The collected organic phases were washed with a saturated aqueous solution of sodium chloride, dried over sodium sulphate and evaporated. The residue was purified by column chromatography using a mixture of ethyl acetate and heptane (2:1 to 4:1) as eluant to give the product 8e (0.18 g, 56%) in the form of a brown powder: melting point 170–171° C.; NMR-$^1$H (DMSO-$d_6$) δ 11.48 (1H, s, NH-1), 7.20 (1H, t, J=7.5 Hz, H-5), 6.97–6.92 (3H, m, H-2', 4' and 6'), 6.62 (1H, s, H-6), 5.49 (2H, s, NH$_2$-3), 2.27 (3H, s, CH$_3$-3'), 1.97 (3H, s, CH$_3$-5). Anal. C$_{13}$H$_{14}$N$_2$O$_3$S (C, H, N, S).

EXAMPLE 21

Preparation of 3-amino-4-(3', 5'-dimethylphenyl)-thio-quinoline-2(1H)-one (compound 8f)

As described for compound 8a in example 17, stannous chloride dihydrate (1.04 g, 4.6 mmoles) was added to a suspension of compound 7f (0.30 g, 0.9 mmoles) in ethyl acetate (10 ml). The mixture was heated at 70° C. for 1 hour. After cooling to 0° C., 10 ml of iced water was added and the solution was made basic with a saturated solution of sodium carbonate. The yellow precipitate was removed by filtration. The filtered phases were separated and the aqueous phase was extracted with 3×10 ml of ethyl acetate. The collected organic phases were washed with a saturated aqueous sodium chloride solution (3×10 ml), dried over magnesium sulphate and concentrated. The solid obtained was crystallised in ethyl acetate to give the product 8f (0.14 g, 52.5%) in the form of green crystals: melting point 235–236° C.; NMR-$^1$H (DMSO-$d_6$) δ 10.01 (1H, s, NH-1), 7.72 (1H, d, J=8 Hz, H-8;), 7.33–7.09 (3H, m, H-5, 6 and 7), 6.80 (1H, s, H-4'), 6.77 (2H, s, H-2' and 6'), 6.06 (2H, s, NH2), 2.18 (6H, s, CH$_3$-3' and 5'). Anal. C$_{17}$H$_{16}$N$_2$OS. 0.25H20 (C, H, N, S).

EXAMPLE 22

Preparation of 3-amino-5-ethoxymethyl-4-(3', 5'-dimethylphenyl)thio-pyridin-2(1H)-one (compound 8q)

Compound 7g (150 mg, 0.45 mmole) was dissolved in absolute ethanol (5 ml). The catalyst (palladium on carbon 10%, 50 mg) was added and the mixture was agitated under a hydrogen atmosphere at ambient temperature for 24 hours. The catalyst was removed by filtration and the solvent was evaporated. The residue was purified by column chromatography using a mixture of dichloromethane and ethanol (1:0 to 96/4) as eluant to give the product 8g (32 mg, 23%) in the form of brown crystals: melting point 149–150° C.; NMR-$^1$H (CDCl$_3$): 12.27 (1H, S broad, NH-1), 6.90 (1H, S, H-6), 6.76 (1H, S, H-4'), 6.73 (2H, S, H-2' and 6'), 4.91 (2H, S, NH$_2$-3), 4.35 (2H, S, CH$_2$O-5), 3.48 (2H, q, J=7H$_2$, CH$_3$ $\underline{CH}_2$O), 2.22 (6H, S, CH$_3$-3' and 5'), 1.14 (3H, t, J=7H$_2$, $\underline{CH}_3$CH$_2$O). Anal. C$_{16}$H$_{20}$N$_2$O$_2$S$_1$ (C, H, N, S).

EXAMPLE 23

Preparation of 5-methyl-3-nitro-4-(4', 6'-dimethylpyrimidin-2-yl)thiopyridin-2(1H)-one (compound 9a)

As described for compound 7a in example 10, a mixture of compound 6a (0.14 g, 0.72 mmole) in 10 ml of ethanol and 0.26 ml of triethylamine (1.80 mmoles) was agitated until homogeneous. 2-mercapto-4,6-dimethylpyrimidine (0.09 g, 0.67 mmole) was added. After 3 hours of agitation under reflux, the solvent was evaporated. 10 ml of water was added and the suspension was agitated at ambient temperature for 1 hour. The solid was isolated by filtration and was dried over $P_2O_5$ under vacuum to give the product 9a (0.12 g, 58%) in the form of a pale yellow solid: melting point 238–239° C.; NMR-$^1$H (DMSO-$d_6$) δ 13.02 (1H, s, NH-1), 7.75 (1H, s, H-6), 7.15 (1H, s, H-5'), 2.36 (3H, s, CH3-4' and 6'), 2.03 (3H, s, CH3-5). Anal. $C_{12}H_{12}N_4O_3S$ . $0.125H_2O$ (C, H, N, S).

EXAMPLE 24

Preparation of 5-methyl-3-nitro-4-(4'-hydroxy-6'-methylpyrimidin-2-yl)thiopyridin-2(1H)-one (compound 9b)

As described for compound 7a in example 10, a mixture of compound 6a (0.50 g, 2.6 mmole) in 20 ml of ethanol and 0.55 ml of triethylamine (4.0 mmoles) was agitated until homogeneous. 4-hydroxy-2-mercapto-6-methylpyrimidine (0.38 g, 2.7 mmole) was added. The suspension was agitated under reflux for 4 hours 30 minutes and at ambient temperature for 15 hours. The solvent was evaporated and 10 ml of water was added. The mixture was made basic with a dilute aqueous ammonia solution and agitated for 2 hours at ambient temperature. The precipitate was removed by filtration. The aqueous phase was neutralised with an aqueous solution of hydrochloric acid and was extracted with 3×150 ml of ethyl acetate. The organic phase was concentrated and the residue purified by column chromatography using a mixture of hexane and ethyl acetate (1:1 to 0:1) and a mixture of ethyl acetate and ethanol (95:5 to 9:1) as eluants to give the product 9b (0.23 g, 30%) in the form of pale green coloured crystals: melting point >350° C.; NMR-$^1$H (DMSO-$d_6$) δ 13.02 (1H, s, NH-1), 7.86 (1H, s, H-6), 6.04 (1H, s, H-5'), 2.22 (3H, s, $CH_3$-6'), 1.90 (3H, s, $CH_3$-5). Anal. $C_{11}H_{10}N_{4O4}S$ (C, H, N, S).

EXAMPLE 25

Preparation of 5-methyl-3-nitro-4-(benzimidazol-2-yl)thiopyridin-2(1H)-one (compound 9c)

As described for compound 7a in example 10, a mixture of compound 6a (0.10 g, 0.5 mmole) in 10 ml of ethanol and 0.11 ml of triethylamine (0.8 mmoles) was agitated until homogeneous. 2-mercaptobenzimidazole (0.08 g, 0.5 mmole) was added and the suspension was agitated under reflux for 6 hours 30 minutes and at ambient temperature for 72 hours. The suspension was agitated at ambient temperature for 3 hours. The yellow solid obtained was isolated by filtration, washed with water and dried over $P_2O_5$ under vacuum to give the product 9c (0.11 g, 66%) in the form of yellow crystals: melting point 272–275° C.; NMR-$^1$H (DMSO-$d_6$) δ 12.93 (1H, s, NH-1), 7.72 (1H, s, H-6), 7.56 (2H, m, H-5' and 8'), 7.25–7.21 (2H, m, H-6' and 7'), 1.88 (3H, s, $CH_3$-5) Anal. $C_{13}H_{10}N_4O_3S$ . $0.25H_2O$ . $0.25C_2H_{50}H$ (C, H, N).

EXAMPLE 26

Preparation of 5-methyl-3-nitro-4-(benzoxazol-2-yl)thiopyridin-2(1H)-one (compound 9d)

As described for compound 7a in example 10, a mixture of compound 6a (0.50 g, 2.6 mmole) in 20 ml of ethanol and 0.55 ml of triethylamine (4.0 mmoles) was agitated until homogeneous. 2-mercaptobenzoxazole (0.40 g, 2.6 mmole) was added and the mixture was agitated under reflux for 3 hours and at ambient temperature for 15 hours. The solvent was evaporated and the residue was crystallised in ethanol to give the product 9d (0.22 g, 27%) in the form of a brown solid: melting point 180–181° C.; NMR-$^1$H (DMSO-$d_6$) δ 8.91 (1H, broad, NH-1), 7.85 (1H, s, H-6), 7.81–7.70 (2H, m, H-5' and 8'), 7.50–7.39 (2H, m, H-6' and 7'), 2.10 (3H, s, $CH_3$-5). Anal. $C_{13}H_9N_3O_4S$ . $0.5C_2H_5OH$ (C, H, N, S).

EXAMPLE 27

Preparation of 5-methyl-3-nitro-4-(benzothiazol-2-yl)thio-pyridin-2(1H)-one (compound 9e)

As described for compound 7a in example 10, a mixture of compound 6a (0.10 g, 0.5 mmole) in 10 ml of ethanol and 10 ml of triethylamine was agitated until homogeneous. 2-mercaptobenzothiazole (0.09 g, 0.5 mmole) was added and the mixture was agitated at ambient temperature for 15 hours and under reflux for 4 hours. All the volatile substances were evaporated and 10 ml of water added. The yellow solid was isolated by filtration, washed with water and dried over $P_2O_5$ under to give the product 9e (0.10 g, 60%) in the form of yellow crystals: melting point 240° C.; NMR-$^1$H (DMSO-$d_6$) δ 12.90 (1H, broad, NH-1), 8.09 (1H, dd, $J_1$=7 Hz, $J_2$=1 Hz, H-8'#), 7.96 (1H, dd, $J_1$=7 Hz, $J_2$=1 Hz, H-5'#), 7.88 (1H, s, H-6), 7.56 (1H, td, $J_1$=7 Hz, $J_2$=1 Hz, H-7'*), 7.47 (1H, td, $J_1$=7 Hz, $J_2$=1 Hz, H-6'*), 2.10 (3H, s, $CH_3$-5). Anal. $C_{13}H_9N_3O_3S_2$ (C, H, N).

EXAMPLE 28

Preparation of 5-methyl-3-nitro-4-(thiazolin-2-yl)thio-pyridin-2(1H)-one (compound 9f)

As described for compound 7a in example 10, a mixture of compound 6a (0.50 g, 2.6 mmole) in 10 ml of ethanol and 20 ml of triethylamine was agitated until homogeneous. 2-mercaptothiazoline (0.32 g, 2.6 mmole) was added and the mixture was agitated under reflux for 8 hours and at ambient temperature for 15 hours. All the volatile substances were evaporated and 20 ml of water added. The suspension was agitated at ambient temperature for 48 hours. The solid was isolated by filtration and washed with water. It was purified by column chromatography using a mixture of dichloromethane and ethanol (1:0 to 9:1) as eluant to give the product 9f (0.05 g, 7%) in the form of brown crystals: melting point 177° C.; NMR-$^1$H (DMSO-$d_6$) δ 13.10 (1H, broad, NH-1), 7.41 (1H, s, H-6), 4.21 (2H, t, J=8 Hz, H-4'), 3.45 (2H, t, J=8 Hz, H-5'), 2.20 (3H, s, $CH_3$-5). Anal. $C_9H_9N_3 O_3S_2$. $0.25C_2H_5OH$ (C, H, N).

EXAMPLE 29

Preparation of 5-methyl-3-nitro-4-(N-methylimidazol-2-yl)thio-pyridin-2(1H)-one (compound 9g)

As described for compound 7a in example 10, a mixture of compound 6a (0.50 g, 2.6 mmoles) in 20 ml of ethanol and 0.55 ml of triethylamine (4.0 mmoles) was agitated until homogeneous. 2-mercapto-1-methylimidazole (0.30 g, 2.6 mmoles) was added and the mixture was agitated under reflux for 6 hours and at ambient temperature for 15 hours. The solvent was evaporated and 15 ml of water added. The suspension was agitated at ambient temperature for 1 hour. The solid was isolated by filtration, washed with water and dried over $P_2O_5$ under vacuum to give the product 9g (0.60 g, 85%) in the form of yellow crystals: melting point 260–265° C.; NMR-$^1$H (DMSO-$d_6$) δ 9.45 (1H, s, NH-1), 7.51 (1H, s, H-6), 7.38 (1H, t, J=1 Hz, H-5'*), 7.04 (1H, d, J=1 Hz, H-4'*), 3.61 (3H, s, N-CH$_3$), 1.82 (3H, s, CH$_3$-5). Anal. $C_{10}H_{10}N_4O_3S$ (C, H, N, S).

EXAMPLE 30

Preparation of 5-methyl-3-nitro-4-(2-pyridyl) thio-pyridin-2(1H)-one (compound 9h)

As described for compound 7a in example 10, a mixture of compound 6a (0.10 g, 0.5 mmoles) in 10 ml of ethanol and 10 ml of triethylamine was agitated until homogeneous. 2-mercaptopyridine (0.06 g, 0.5 mmoles) was added and the mixture was agitated at ambient temperature for 48 hours. The solvent was evaporated and 10 ml of water added. The suspension was agitated at ambient temperature for 3 hours. The solid was isolated by filtration, washed with water and dried over $P_2O_5$ under vacuum to give the product 9h (0.09 g, 66%) in the form of brown crystals: melting point 195–196° C.; NMR-$^1$H (DMSO-$d_6$) δ 12.89 (1H, broad, NH-1), 8.47–8.44 (1H, m, H-6'), 7.85–7.76 (1H, m, H-4'), 7.73 (1H, s, H-6), 7.41–7.28 (2H, m, H-3' and 5'), 1.93 (3H, s, CH$_3$-5). Anal. $C_{11}H_9N_3O_3S$ (C, H, N, S).

EXAMPLE 31

Preparation of 3-amino-5-methyl-4-(benzoxazol-2-yl)thio-pyridin-2(1H)-one (compound 10)

As described for compound 8a in example 17, stannous chloride dihydrate (420 mg, 1.9 mmoles) was added to a suspension of compound 9d (110 mg, 0.4 mmoles) in ethyl acetate (10 ml). The mixture was heated under reflux for 6 hours. After cooling to 0° C., 10 ml of iced water was added and the solution was made basic with a saturated solution of sodium carbonate. The two phases were separated and the aqueous phase was extracted with 3×20 ml of ethyl acetate. The collected organic phases were washed with a saturated aqueous sodium chloride solution (3×10 ml), dried over magnesium sulphate and concentrated. The residue was washed with dichloromethane to give the product 10 (10 mg, 10%) in the form of a brown solid : melting point 296–297° C.; NMR-$^1$H (DMSO-$d_6$) δ 11.36 (1H, s broad, NH-1), 9.98 (1H, s, NH$_2$-3), 9.83 (1H, s, NH$_2$-3), 8.35 (1H, d, J=7 Hz, H-5'*), 6.99 (1H, s, H-6), 6.94–6.82 (3H, m, H-6', 7' and 8'*), 2.16 (3H, s, CH$_3$-5). Anal. $C_{13}H_{11}N_3O_2S \cdot H_2O$ (C, H, N).

EXAMPLE 32

Preparation of 3-formamido-5-methyl-4-(3', 5'-dimethylphenyl)thio-pyridin-2(1H)-one (compound 11a)

Formic acid (2 ml) was added to a solution of amine 8a (0.10 g, 0.4 mmole) in ethyl formate (previously distilled over calcium hydride) (8 ml). The mixture was heated under reflux for 12 hours. After evaporation of the volatile substances, the residue was washed twice with ethanol and once with ethyl acetate. It was purified by column chromatography using a mixture of dichloromethane and ethanol (95:5) as eluant and, at the end, ethyl acetate, to give compound 11a (0.06 g, 58%) in the form of a white powder: melting point 221–222° C.; NMR-$^1$H (DMSO-$d_6$) δ 11.96 (1H, s, NH-1), 8.28 (1H, s, NH-3) 7.23 (1H, s, H-6), 6.88 (1H, d, H-4'), 6.78 (2H, s, H-2' and 6'), 2.23 (6H, s, CH$_3$-3' and 5'), 1.85 (3H, s, CH$_3$-5). Anal. $C_{15}H_{16}N_2O_2S$ (C, H, N, S).

EXAMPLE 33

Preparation of 3-acetamido-5-methyl-4-(3', 5'-dimethylphenyl)thio-pyridin-2(1H)-one (compound 11b)

A solution of the amine 8a (0.10 g, 0.4 mmole) and acetic anhydride (0.05 ml, 0.39 mmole) in acetic acid (20 ml) was heated under reflux for 1 hour 30 minutes. After evaporation of the solvents, 10 ml of water was added and the mixture was neutralised at 0° C. with a dilute aqueous solution of ammonia. After filtration, the residue was washed with cyclohexane (2×5 ml). Product 11b was obtained (0.10 g, 86%) in the form of a pale beige solid: melting point 138° C.; NMR-$^1$H (DMSO-$d_6$) δ 11.84 (1H, s, NH-1), 9.41 (1H, s, NH-3), 7.20 (1H, s, H-6), 6.87 (1H, s, H-4'), 6.81 (2H, s, H-2' and 6'), 2.22 (6H, s, CH$_3$-3' and 5'), 1.99 (3H, s, CH$_3$-5), 1.81 (3H, s, CH$_3$CO). Anal. $C_{16}H_{18}N_2O_2S \cdot H_2O$ (C, H, N, S).

EXAMPLE 34

Preparation of 5-methyl-3-propionamido-4-(3', 5'-dimethylphenyl)thio-pyridin-2(1H)-one (compound 11c)

Freshly distilled propionyl chloride (0.04 ml, 0.41 mmole) (the receptacle is fitted with a trap containing $CaCl_2$) was added to a solution of amine 8a (0.10 g, 0.40 mmole) and triethylamine (0.04 ml, 0.38 mmole) in dichloromethane (5 ml) at 0° C. The mixture was agitated at ambient temperature for 5 hours. The solvent was evaporated, water was added and the solid was isolated by filtration. The residue was purified by column chromatography using a mixture of dichloromethane and ethanol (94:6) as eluant and at the end ethyl acetate in order to obtain the compound 11c (0.10 g, 90%) in the form of a white powder: melting point 186–188° C.; NMR-$^1$H (DMSO-$d_6$) δ 11.86 (1H, s, NH-1), 8.60 (1H, s, NH-3), 7.21 (1H, s, H-6), 6.88 (1H, s, H-4'), 6.80 (2H, s, H-2' and 6'), 4.04 (2H, q, J=7 Hz, COCH$_2$CH$_3$), 2.22 (6H, s, CH$_3$-3' and 5'), 1.82 (3H, s, CH$_3$-5), 1.20 (3H, t, J=7 Hz, COCH$_2$CH$_3$). Anal. $C_{17}H_{20}N_2O_2S \cdot 1.25H_2O$ (C, H, N, S).

EXAMPLE 35

Preparation of 3-heptanamido-5-methyl-4-(3', 5'-dimethylphenyl)thio-pyridin-2(1H)-one (compound 11d)

A solution of amine 8a (100 mg, 0.38 mmole) and heptanoic anhydride (0.14 g, 0.58 mmole) in toluene (4 ml) was heated at 100° C. for 1 hour 30 minutes. After evaporation of the toluene, 5 ml of diethyl ether was added. Once the precipitate had been obtained, the solvent was removed using a pipette. The solid was washed twice in this way with diethyl ether. After filtration, the residue was recrystallised in ethyl acetate. Product 11d was obtained (17 mg, 50%) in the form of yellow micro-crystals: melting point 212–213° C.; NMR-$^1$H (DMSO-$d_6$) δ 11.86 (1H, s, NH-1), 9.34 (1H, s, NH-3), 7.19 (1H, s, H-6), 6.86 (1H, s, H-4'), 6.76 (2H, s, H-2' and 6'), 2.28 (2H, t, J=7 Hz, COCH$_2$), 2.22 (6H, s, CH$_3$-3' and 5'), 1.81 (3H, s, CH$_3$-5), 1.53 (2H, dd, J=7 Hz, COCH$_2$CH$_2$), 1.28–1.21 (6H, m, (CH$_2$)$_3$), 0.86 (3H, t, J=6.5 Hz, (CH$_2$)$_5$CH$_3$). Anal. $C_{21}H_{28}N_2O_2S$ (C, H, N, S).

EXAMPLE 36

Preparation of 5-methyl-3-phenylacetamido-4-(3', 5'-dimethylphenyl)thio-pyridin-2(1H)-one (compound 11e)

A molar equivalent of triethylamine (0.035 ml, 0.25 mmole) was added to a suspension of amine 8a (65 mg, 0.25 mmole) in dichloromethane (5 ml). A distilled solution of phenylacetyl chloride (39 mg, 0.25 mmole) in dichloromethane (1 ml) was added drop by drop to this mixture cooled in iced water. The mixture was agitated at ambient temperature for 2 hours. After evaporation of the solvent, 10 ml of water was added. After filtration, the residue was purified by column chromatography using a mixture of dichloromethane and ethanol (95:5) as eluant. Product 11e was obtained (53 mg, 56%) in the form of green crystals: melting point 200–202° C.; NMR-$^1$H (DMSO-$d_6$) δ 11.88 (1H, s, NH-1), 9.67 (1H, s, NH-3), 7.37–7.21 (5H m, $C_6H_5$), 6.87 (1H, s, H-4'), 6.76 (2H, s, H-2' and 6'), 3.67 (2H, s, $CH_2$), 2.22 (6H, s, $CH_3$-3' and 5'), 1.80 (3H, s, $CH_3$-5). Anal. $C_{22}H_{22}N_2O_2S$ (C, H, N).

EXAMPLE 37

Preparation of 5-methyl-3-N-ethoxycarbamoyl-4-(3', 5'-dimethylphenyl)thio-pyridin-2(1H)-one (compound 11f)

Triethylamine (0.10 g, 0.50 mmole) was added to a solution of amine 8a (0.05 g, 0.20 mmole) in ethanol (2 ml). Freshly distilled ethyl chloroformate (0.65 g, 6.00 mmoles) was added drop by drop to this mixture cooled in iced water. The mixture was agitated at ambient temperature for 48 hours. After evaporation of the solvent, 5 ml of water was added. After filtration, the red solid was purified by column chromatography using a mixture of dichloromethane and ethanol (98:2) as eluant to give the recovered amine 8a (0.005 g, 10%) and the compound 11f (0.01 g, 26%) in the form of a white solid: melting point 208–210° C.; NMR-$^1$H (DMSO-$d_6$) δ 11.83 (1H, s, NH-1), 8.60 (1H, s, NH-3), 7.21 (1H, s, H-6), 6.88 (1H, s, H-4'), 6.80 (2H, s, H-2' and 6'), 4.04 (2H, q, J=7 Hz O$CH_2$CH$_3$), 2.22 (6H, s, $CH_3$-3' and 5'), 1.82 (3H, s, $CH_3$-5), 1.19 (3H, t, J=7 Hz, OCH$_2CH_3$) Anal. $C_{17}H_{20}N_2O_3S$ (C, H, N, S).

EXAMPLE 38

Preparation of 3-acetamido-5-ethyl-6-methyl-4-(3', 5'-dimethylphenyl)thio-pyridin-2(1H)-one (compound 11q)

A solution of amine 8c (0.20 g, 0.7 mmole) and acetic anhydride (0.09 ml, 0.9 mmole) in acetic acid (40 ml) was heated under reflux for 5 hours 30 minutes. After evaporation of the solvents, 20 ml of iced water was added and the mixture neutralised at 0° C. with a dilute aqueous solution of ammonia. The mixture was agitated at ambient temperature overnight. After filtration, the residue was washed with cyclohexane (2×10 ml). Product 11g was obtained (0.17 g, 74%) in the form of a light brown solid: melting point 238–239° C.; NMR-$^1$H (DMSO-$d_6$) δ 11.90 (1H, s broad, NH-1), 9.18 (1H, s broad, NH-3), 6.83 (1H, s, H-4'), 6.77 (2H, s, H-2' and 6'), 2.22 (9H, s, $CH_3$-5, 3' and 5'), 1.87 (3H, s, $CH_3$CO), 0.85 (3H, t, J=7 Hz, $CH_3$CH$_2$). The signal from $CH_3$CH$_2$ and the signal from the DMSO overlap one another. Anal. $C_{18}H_{22}N_2O_2S$ . 0.45$H_2O$ (C, H, N, S).

EXAMPLE 39

Preparation of 4-chloro-5-ethyl-6-methyl-3-carbethoxy-pyridin-2(1H)-one (compound 14)

As for the method described for obtaining compound 6a described by Nguyen et al. (1992, previously quoted), phosphorus oxychloride (5.4 ml, 56.8 mmoles) was added to a solution of compound 13 (3.00 g, 13.3 mmoles) and benzyltriethylammonium chloride (12.12 g, 53.2 mmoles) in acetonitrile (60 ml). The mixture obtained was heated under reflux for 6 hours to give a red solution. After evaporation of the solvent, 20 ml of iced water was added and the mixture agitated at 0° C. for 4 hours. The precipitate was collected, washed with cyclohexane (2×4 ml) and crystallised in ethyl acetate to give compound 14 (2.3 g, 71%) in the form of white crystals: melting point 167° C.; NMR-$^1$H (DMSO-$d_6$) δ 12.24 (1H, s, NH-1), 4.28 (2H, q, j=7 Hz, COO$CH_2$CH$_3$), 2.31 (3H, s, $CH_3$-6), 1.29 (3H, t, j=7 Hz, COOCH$_2CH_3$), 1.06 (3H, t, j=7 Hz, CH$_2CH_3$), the signal from CH$_2CH_3$ and the signal from the DMSO overlap one another. Anal. $C_{11}H_{14}NO_3Cl$ (C, H, N, Cl).

EXAMPLE 40

Preparation of 5-ethyl-6-methyl-3-carbethoxy-4-(3', 5'-dimethylphenyl)thio-pyridin-2(1H)-one (compound 15)

As for the method described for obtaining compound 7a in example 10, a mixture of compound 15 (1.00 g, 4.1 mmoles) in 10 ml of ethanol and 1 ml of triethylamine was agitated until homogeneous. 3,5-dimethylthiophenol (0.61 ml, 4.5 mmoles) was added. After 12 hours under reflux, the white precipitate was isolated by filtration and crystallised in ethyl acetate. Product 15 was obtained (1.05 g, 82%) in the form of white crystals: melting point 202° C.; NMR-$^1$H (DMSO-$d_6$) δ 12.17 (1H, s, NH-1), 7.22 (1H, s, H-4'), 6.92 (1H, s, H-2' and 6'), 4.09 (2H, q, J=7 Hz, COO$CH_2$CH$_3$), 2.45 (2H, q, J=7 Hz, $CH_2$CH$_3$), 2.27 (3H, s, $CH_3$-6), 2.25 (6H, s, $CH_3$-3' and 5'), 1.15 (3H, t, j=7 Hz, COOCH$_2CH_3$), 0.85 (3H, t, J=7 Hz, CH$_2CH_3$). Anal. $C_{19}H_{23}NO_3S$ (C, H, N, S).

EXAMPLE 41

Preparation of 5-ethyl-6-methyl-4-(3', 5'-dimethylphenyl)thio-pyridin-2(1H)-one (compound 16)

Compound 15 was dissolved (120 mg, 0.34 mmole) in 6 ml of a mixture of tetrahydrofuran, H$_2$O and HCl at 37% (18:3:4). The mixture was agitated at 75° C. for 10 days. The tetrahydrofuran was evaporated and 5 ml of water added. The mixture was agitated and the water removed. The residue was crystallised in ethanol (25 ml) to give the product 16 (50 mg, 59%) in the form of colourless flakes: melting point 277–278° C.; NMR-$^1$H (DMSO-$d_6$) δ 11.26 (1H, s, NH-1), 7.22 (3H, s, H-2', 4' and 6'), 5.25 (1H, s, H-3), 2.36 (6H s, $CH_3$-3' and 5'), 2.21 (3H, s, $CH_3$-6), 1.13 (3H, t, J=7.5 Hz, CH$_2CH_3$). The signal from $CH_2$CH$_3$ and the signal from the DMSO overlap one another. Anal. $C_{16}H_{19}NOS$ . 0.25$H_2O$ (C, H, N, S).

EXAMPLE 42

Biological activity of the compounds according to the invention

1°) Equipment and Methods

Evaluation of the Antiviral Activity of the Compounds

The effects of the compounds were evaluated on the replication of HIV-1 (see Table 2) on CEM-SS cells (cell lines of the lymphocytic lineage) strongly infected with HIV-1 LAI as described by Moog et al. (Antiviral Research (1994), 24, 275–288). The CEM-SS and the HIV-1 resistant to Nevirapine (N119) carrying a point mutation at codon 181 of the IT, were supplied respectively by P. NARA and D. RICHMAN through the intermediary of the AIDS Research and Reference Reagent Program, Division of AIDS, NIAID, NIH (USA) (Catalogue references: No. 776 and No. 1392).

The virus production was measured by quantifying the activity of the inverse transcriptase associated with viral particles released into the culture supernatant. In short, cells were infected with 100 $TCID_{50}$ for 30 minutes; after adsorption of the virus, unbound particles were removed by two washings and the cells were cultivated in the presence of different concentrations of the compounds tested for 5 days before determining the viral production. The concentration inhibiting 50% of the viral multiplication ($IC_{50}$) came from the computer plot of the median effect of the dose effect results (Chou et al. Elsevier Science Publishers, Cambridge U.K. (1985), 19–28).

In parallel experiments, the cytotoxicity of the molecules was measured on non-infected cells, after an incubation of 5 days in the presence of these molecules, by using a calorimetric titration (MTT test) based on the ability of the mitochondrial dehydrogenases of the living cells to reduce 3-(4,5-dimethylthiazol-2-yl)-2,5-diphenyltetrazolium bromide in formazan (Mosmann et al. J. Immunol. Methods (9183), 65, 55–63). The concentration cytotoxic at 50% ($CC_{50}$) is the concentration at which the $DO_{540}$ has been reduced to half and is calculated by using the program mentioned above.

Expression and Purification of the IT Enzyme of Recombinant HIV-1

Yeast cells transformed with the pAB 24/IT-4 vector were used to purify the IT enzyme of the recombinant HIV-1 as described by Sallafranque-Andreola et al. (1989 Eur. J. Biochem. 184, 364–374).

The system for the expression of the IT of HIV-2 in *E.coli* (B. Muller et al. (1991 J. Biol. Chem. 266, 14708–14713) was provided by Dr. R. Goody. The IT of the HIV-2 was purified in the same way as the IT of the HIV-1.

Determination of Inverse Transcriptase

Incubation was carried out at 37° C. for 10 minutes in the presence of various matrix-primers.

a) Poly C-oligo dG: the reaction mixture contained a final volume of 0.05 ml, Tris-HCl 50 mM pH 8.0, $MgCl_2$ 5 mM, dithiothreitol 4 mM, 0.48 $A_{260}$/ml of poly C-oligo dG (5:1), 1.0 μCi of [$^3$H]dGTP (28 Ci/mmole), dGTP 2 μM, KCl 80 mM, 1 μg of bovine serum albumin and IT 20–50 nM.

b) Poly A-oligo dT: the same conditions as in a), except that 0.48 $A_{260}$/ml of poly A-oligo dT (5:1), 0.5 μCi of [$^3$H]dTTP (46 Ci/mmole), dTTP 20 μM were used.

The reactions were stopped by adding in the cold 1 ml of 10% trichloroacetic acid plus sodium pyrophosphate 0.1 M. The precipitates were filtered through nitrocellulose membranes, washed with 2% trichloroacetic acid, dried and counted in a PPO/POPOP/toluene scintillation mixture.

Inverse Transcription

The pmCG6 plasmid containing the nucleotide fragment 1–4005 of the HIV-1 (pmal) in psP64, under the control of the promoter of the T7 bacteriophage was provided by Dr. J. L. Darlix. A strain of *E.coli* HB 101 (1035) recA was used for the amplification of the plasmid. After digestion of this clone with Hinc II and transcription in vitro by using the RNA T7 polymerase, RNAs were obtained from the +50 position of the pmal sequence. The transcription was carried out in vitro and the inverse transcription in the manner described by B. Bordier et al. (1992 Nucleic Acids Res. 20, 5999–6006).

Inhibition Experiments

All the compounds were dissolved in dimethyl#sulphoxide (DMSO). The test samples were prepared in the presence of the same final concentration of DMSO. $IC_{50}$ is the concentration required to inhibit the activity of the IT of the recombinant HIV-1 by 50%.

2°) Results

Inhibition of the Multiplication of HIV-1

Thirty two compounds according to the invention were studied for their anti-HIV-1 biological activity. Several molecules showed important antiviral properties (see Table 2). Among the best inhibitors showing a selectivity index greater than 20, several were tested on a colony resistant to Neviparine (see Table 3). It was shown that compound 7c retained good anti-HIV-1 activity with an $IC_{50}$ of 260 nM on this resistant colony. This compound was then tested with other colonies and other cell lines (Table 4).

Inhibition of the Inverse Transcriptase

The compounds that did not show activity against HIV-1 in a cell culture were tested on an IT of recombinant HIV-1. The concentration inhibiting 50% of the IT activity ($IC_{50}$) for each compound is given in Table 5. The compounds 7c and 8c were the best inhibitors with $IC_{50}$ values respectively of 30 nM and 15 nM. A derivative of HEPT, 1-benzyloxymethyl-6-(phenylthio)thymine or BPT (Baba et al., Proc. Natl. Acad. Sci. USA, 1991, 88, 2356–2360) tested under the same conditions and used as a reference compound for non-nucleosidic inhibitors gave an $IC_{50}$ value of 400 nM.

Complementary studies have been undertaken to elucidate the nature of the inhibition. These studies were carried out mainly with compounds 7c and 8c.

The IT inhibition was determined by using various matrix-primer couples. It is known that non-nucleosidic IT inhibitors show different levels of inhibition according to the matrix-primer used to measure the IT activity (De Clercq et al. (1993) Medicinal Research Reviews, 13, 229–258).

The dose-response curves for compound 7c in the presence of two different matrix-primers are shown in FIG. 9. Better inhibition was obtained in the presence of poly C-oligo dG compared with poly A-oligo dT. Compound 8c gave the same result. A strong inhibition was also obtained by using RNA from HIV-1 as a natural matrix (FIG. 10).

All the non-nucleosidic inhibitors identified up to now are specific to HIV-1 and do not inhibit the IT of HIV-2. Compounds 7c and 8c were tested with these two IT. As shown in FIG. 9, at the concentrations at which the IT of HIV-1 was well inhibited, the activity of the IT of HIV-2 was not affected. This discriminatory behaviour towards the IT of HIV-1 compared with the IT of HIV-2 is a common property of non-nucleosidic inhibitors.

Enzymatic kinetic analyses showed that the inhibition of the IT of HIV-1 by compounds 7c (or 8c) is non-competitive as regards the dGTP substrate in the presence of the poly C-oligo dG matrix-primer couple (FIG. 12). When poly A-oligo dT was used as a matrix-primer couple, a competitive type of inhibition was obtained (FIG. 13).

EXAMPLE 43

Study of the Permeability of the isolated virion to the inhibitors of the inverse transcriptase of HIV-1

1. Equipment and Methods 1.1 Preparation of Viral Supernatants

H9 cells chronically infected with HIV-1LAI ($10^8$/ml) were cocultivated with MT4 cells ($10^8$/ml) for 48 hours in an RMPI medium supplemented by 10% of calf foetal serum (CFS). The cells were then removed by centrifugation and then the supernatant liquid was filtered (0.45 μm) to remove residual cells and cell debris.

1.2 Separation of the Viral Particles

After having been incubated with the various inhibitors, the viral supernatants (200 μl) were deposited in the filtering part of a VectaSpin tube (WHATMAN) fitted with an ANAPORE membrane of porosity 0.02 μm. For 10 minutes they were subjected to centrifugation, the acceleration of which reached 6000 g at the filtering membrane. The viral residuums thereby obtained (10–15 μl) were washed 3 times under the same conditions with 500 μl of RPMI then restored to their initial volumes with RPMI containing 10% of CFS.

1.3. Cell Culture:

The HT4LacZ-1 cells were kept in a DMEM medium (glucose 4.5 g/l) supplemented with 10% of calf foetal serum in the presence of Gentamycin (50 mg/l). These cells stemmed from Hela cells in which had been cloned, on the one hand the gene coding for the human CD4 so as to render them susceptible to infection by the HIV (Chesebro and Wehrly, 1988, J. Virol., 62, 3779–3788), and on the other hand the gene for β-Galactosidase which, placed under the dependent of the LTR of the HIV-1 served as a marker for the viral infection (Rocancourt et al. (1990) J. Virol. 1990 64–6, 2660–2688). When the virus infects such cells after its integration into the cellular genome, the production of the regulatory protein TAT activates the LTR of the HIV. The result is an activation of the gene of β-Galactosidase which leads to its production in the intracellular medium and more particularly in the nucleus. It is this protein that serves as a marker of the infection.

1.4 Measurement of the Infectivity:

The evening of day 0, the HT4LacZ-1 cells were diluted at the rate of 75000 cells per ml of medium. 100 μl of this suspension was then distributed over a flat bottomed plate with 96 wells and was cultivated overnight at 37° C. (5% of $CO_2$).

The morning of day 1, the supernatant liquid was removed by aspiration. Each well was then complemented with 200 μl of the viral supernatant dilutions to be tested. Each dilution was made in a DMEM medium (glucose 4.5 g/l) supplemented with 10% of CFS. The plates were then placed in an environment at 37° C. in the presence of 5% of $CO_2$.

After 48 hours of culture, the supernatant liquid was aspirated, then each well was washed 3 times in PBS before being complemented with 200 μl of developing buffer (Tris-HCl 50 mM pH=8.5, ONPG 5 mg/ml β-mercaptoethanol 7 μl/ml Tritonx100 0.05%). After 4 hours of incubation at 37° C., the optical density of each well was measured.

2. Results 2.1 Validation of the Viral Ultrafiltration

The procedure described above was applied to a viral supernatant stemming from a H9-MT4 co-culture. After each centrifugation, the viral residuum was taken up in its initial volume using RMPI 16/40 medium containing 10% of calf foetal serum, and then an aliquot was taken for the purposes of analysis (the initial volume of successive centrifugations being modified, the volume of washing was readjusted at each step). Three viral concentrates and three filtrates were thus obtained. These were analysed, on the one hand by measuring the inverse transcriptase activity (reflecting the quantity of virus present) and on the other hand by measuring their infective power (depending directly on the integrity of each particle).

2.1.1 Measurement of the inverse transcriptase (IT) activity

Each of the concentrates of viral filtrates readjusted to their initial volume was analysed with regard to its IT activity. To do this, 50 μl of supernatant was tested in the presence of a duplex matrix/primer made up of poly rA and oligo dT in the presence of dTTP-$H^3$. The results are described in FIG. 14.

The IT activity measurements of the three concentrates showed a loss in activity of the order of 5% after three filtrations. The observed values in the three filtrates merged with the background noise, indicating the excellent homogeneity of the ANOPORE membranes 2.1.2. Measurement of Infectiveness So as to evaluate the possible toxicity of the process on the viral particle, measurements of infectivity were carried out. To do this, various dilutions of the viral concentrates were brought into contact with the MT2 cells in 200 μl of the RMPI medium supplemented with 10% of calf foetal serum. After 3 hours of incubation, the cells were washed twice then put back into culture for 96 hours. After this time, the supernatant was sampled, the cells removed by centrifugation, then the supernatant liquid was tested with regard to its inverse transcriptase activity. The results shown in FIG. 15 showed that the infectious power was not significantly affected by the ultrafiltration steps.

Ultrafiltration on an ANOPORE 0.02 μ membrane therefore permits rapid, effective and non-traumatising separation of the viral particles.

2.2 activity of the inhibitors of the IT of the HIV-1 on the isolated virion.

The concentration of each of the inhibitors of the IT of the HIV-1 was adjusted to 50 mM in DMSO. The later dilutions were carried out on RPMI 1640. 2 μl of suitable dilutions of each of these inhibitors were added to 198 μl of a freshly unfrozen viral suspension. After 3 hours of incubation at ambient temperature, these suspensions were filtered on 0.02 μ VecraSpin tubes, then washed 3 times with 500 μl of RPMI 1640. The viral residuums were then adjusted to 200 μL with the culture medium (RPMI-10% CFS), then tested with regard to their infectivity on HT4LacZ cells.

The results presented in Table 6 clearly show that except for compound 7c none of the inhibitors showed themselves as active on the isolated virion. So as to verify that these effects were not due to possible degradation, each of these inhibitors had been simultaneously evaluated on HT4LacZ cells in the presence of virus. All showed activities comparable to those described in the literature. The results obtained for Nevirapine at 10 and 1 μM, in the current state of experimentation are probably linked to experimental fluctuations. It must be added in addition that significant inhibitions in infectivity have been observed with the TIBO R82913 at a concentration of 100 μM. Be that as it may, only compound 7c shows itself to be truly active on the isolated virion at concentrations going down to 100 μM.

2.3 Inhibition of the IT on the Isolated Virion

So as to verify that the inhibition of the infectivity was really due to the anti-inverse transcriptase activity of compound 7c, we measured the IT activity on a poly rA/oligo dT matrix primer after the isolated virions had been incubated 3 hours with this compound.

Compound 7c appeared to penetrate the envelope and the viral capsid to fix itself onto the IT and to block its activity.

On the other hand, preliminary experiments on the kinetics of the penetration of compound 7c indicated that incubations of 45 minutes are sufficient to induce inhibitions in infectivity greater than 98%.

3. Conclusion

These results show that the main inhibitors used in human clinical treatment are totally inactive on the isolated virion (AZT, d4T, 3TC, ddl. TIBO R82913, HEPT NEVIRAPINE). The compound of formula 7c has shown itself capable, after having penetrated the viral particle, of inhibiting the inverse transcriptase and of suppressing the viral infectivity.

This compound therefore behaves as a completely original compound with regard to its ability to penetrate into the isolated virion.

TABLE 1

Elemental analyses of the compounds according to the invention

| Compound | Calculated % | | | | Measured % | | | |
| --- | --- | --- | --- | --- | --- | --- | --- | --- |
| | C | H | N | S | C | H | N | S |
| 4c | 62.74 | 7.19 | 9.15 | | 62.62 | 7.23 | 9.15 | |
| 5b | 44.57 | 4.54 | 14.85 | | 44.83 | 4.25 | 14.69 | |
| 5c | 48.48 | 5.09 | 14.14 | 32.29 | 48.89 | 4.67 | 14.29 | |
| 5g | 52.44 | 2.93 | 13.59 | | 52.45 | 2.94 | 13.56 | |
| 7a | 57.04 | 4.92 | 9.50 | 10.85 | 57.22 | 5.10 | 9.57 | 10.60 |
| 7b | 59.17 | 5.26 | 9.20 | 10.58 | 58.96 | 5.51 | 9.26 | 10.51 |
| 7c | 60.34 | 5.66 | 8.80 | 10.08 | 60.08 | 5.77 | 8.83 | 10.00 |
| 7d | 54.38 | 3.85 | 10.63 | 12.34 | 54.49 | 3.88 | 10.63 | 12.10 |
| 7e | 55.60 | 4.49 | 9.98 | 11.42 | 55.88 | 4.53 | 10.03 | 11.70 |
| 7f | 62.56 | 4.32 | 8.58 | 9.82 | 62.58 | 4.44 | 8.42 | 9.83 |
| 7g | 57.48 | 5.39 | 8.38 | 9.58 | 57.29 | 5.11 | 8.31 | 9.55 |
| 8a | 64.59 | 6.20 | 10.76 | 12.31 | 64.40 | 6.11 | 10.68 | 12.15 |
| 8b | 64.60 | 6.69 | 10.04 | 11.50 | 64.53 | 6.59 | 10.38 | 11.41 |
| 8c | 66.62 | 6.94 | 9.72 | 11.12 | 66.37 | 6.77 | 9.65 | 10.81 |
| 8e | 62.27 | 5.79 | 11.18 | 12.77 | 62.63 | 5.55 | 11.03 | 12.52 |
| 8f | 67.86 | 5.53 | 9.31 | 10.66 | 67.86 | 5.50 | 9.24 | 10.61 |
| 8g | 83.13 | 6.62 | 9.20 | 10.53 | 83.31 | 6.58 | 9.09 | 10.46 |
| 9a | 48.93 | 4.19 | 19.02 | 10.89 | 49.17 | 4.45 | 18.72 | 10.78 |
| 9b | 44.89 | 3.43 | 19.04 | 10.90 | 45.06 | 3.52 | 18.89 | 10.62 |
| 9c | 50.94 | 3.80 | 17.60 | | 50.99 | 3.99 | 17.83 | |
| 9d | 51.53 | 3.71 | 12.88 | 9.83 | 51.31 | 3.91 | 13.17 | 9.86 |
| 9e | 48.89 | 2.84 | 13.16 | | 48.64 | 3.06 | 12.88 | |

| Compound | Calculated % | | | | | Measured % | | | | |
| --- | --- | --- | --- | --- | --- | --- | --- | --- | --- | --- |
| | C | H | N | S | Cl | C | H | N | S | Cl |
| 9f | 40.34 | 3.74 | 14.86 | | | 40.63 | 3.43 | 15.16 | | |
| 9g | 45.11 | 3.79 | 21.04 | 12.04 | | 45.36 | 4.02 | 20.89 | 11.87 | |
| 9h | 50.18 | 3.45 | 15.96 | 12.18 | | 50.01 | 3.74 | 15.68 | 11.94 | |
| 10 | 53.60 | 4.46 | 14.43 | | | 53.82 | 4.19 | 14.18 | | |
| 11a | 62.46 | 5.55 | 9.71 | 11.12 | | 62.19 | 5.49 | 9.62 | 10.91 | |
| 11b | 59.99 | 6.24 | 8.74 | 9.99 | | 59.65 | 6.05 | 8.62 | 9.87 | |
| 11c | 60.27 | 6.65 | 8.27 | 9.45 | | 60.56 | 6.55 | 8.23 | 9.25 | |
| 11d | 67.71 | 7.58 | 7.52 | 8.60 | | 67.57 | 7.68 | 7.27 | 8.46 | |
| 11e | 69.87 | 5.86 | 7.40 | 8.44 | | 70.04 | 5.77 | 7.38 | 8.59 | |
| 11f | 61.45 | 6.02 | 8.43 | 9.64 | | 61.35 | 6.06 | 8.13 | 9.51 | |
| 11g | 63.86 | 6.82 | 8.27 | 9.47 | | 63.69 | 6.58 | 8.28 | 9.60 | |
| 12 | 61.12 | 9.62 | 8.91 | 20.35 | | 61.12 | 9.46 | 8.75 | 20.75 | |
| 13 | 58.66 | 6.71 | 6.22 | | | 58.47 | 6.51 | 6.36 | | |
| 14 | 54.21 | 5.75 | 5.75 | | 14.58 | 54.46 | 5.67 | 5.57 | | 14.77 |
| 15 | 66.09 | 6.67 | 4.06 | 9.27 | | 65.81 | 6.63 | 3.93 | 9.24 | |
| 16 | 69.19 | 7.03 | 5.04 | 11.53 | | 69.58 | 7.19 | 5.05 | 11.41 | |

TABLE 2

Anti-HIV-1 activity of the compounds according to the invention

| Compound | IC$_{50}$ (nM) | CC$_{50}$ (nM) | SI |
| --- | --- | --- | --- |
| AZT | 3 | >100000 | >33333 |
| 7a | 120 | >10000 | >83 |
| 7b | =90 | >10000 | >111 |
| 7c | =6 | >10000 | >1666 |
| 7d | >10000 | >10000 | — |
| 7e | 2800 | >10000 | >3 |
| 7f | 3800 | >100000 | >26 |
| 7g | 5 | >10000 | >2000 |
| 8a | 10 | >10000 | >1000 |
| 8b | 10 | >10000 | >1000 |
| 8c | 14 | >10000 | >714 |
| 8e | 1400 | 78000 | >55 |
| 8f | 250 | >9000 | >36 |
| 8g | 20 | >10000 | >500 |
| 9a | 17500 | 19500 | >1 |
| 9b | >100000 | >100000 | — |
| 9c | 43500 | 54500 | >1 |
| 9d | 5500 | 16000 | >2 |
| 9e | 14500 | 13500 | — |
| 9f | 17000 | 21500 | >1 |
| 9g | 56000 | 68500 | >1 |
| 9h | 18000 | 28500 | >1 |
| 10 | 8000 | 7500 | — |
| 11a | 6600 | >100000 | >15 |
| 11b | 67 | >100000 | >1492 |
| 11c | 41400 | >100000 | >2 |
| 11d | >10000 | >10000 | — |
| 11e | >10000 | >10000 | — |
| 11f | 7500 | >100000 | >13 |
| 11g | 50 | >80000 | >1600 |
| 15 | 3 | >10000 | >3333 |
| 16 | 500 | >10000 | >20 |

TABLE 3

Anti-HIV-1 activity of compounds according to the
invention against a strain resistant to Nevirapine

| Compound | IC$_{50}$ (nM) | CC$_{50}$ (nM) | SI |
|---|---|---|---|
| TIBO R82913* | >10000 | >10000 | — |
| 7a | >10000 | >10000 | — |
| 7b | 6700 | >10000 | >1 |
| 7c | 260 | >10000 | >38 |
| 7f | >10000 | >10000 | — |
| 8a | >10000 | >10000 | — |
| 8b | 6700 | >10000 | >1 |
| 8c | 2100 | >10000 | >4 |
| 8e | 41500 | 78000 | >1 |
| 8f | 6600 | 8200 | >1.5 |
| 11b | >100000 | >100000 | — |
| 11g | 4300 | >100000 | >23 |
| 15 | 2200 | >10000 | >4.5 |

*TIBO R82913: 4,5,6,7-tetrahydro-5-methyl-imidazo[4,5,1-jk][1,4-]-benzodiazepin-2(1H)-one

TABLE 4

Anti-HIV-1 and anti-HIV-2 activity of compound 7c

| | IC$_{50}$ (M) | CC$_{50}$ (M) |
|---|---|---|
| HIV-1 (LA1)/CEMSS | <4 × 10$^{-10}$ | >10$^{-5}$ |
| AZT (LA1)/CEMSS | 8.4 × 10$^{-10}$ | |
| HIV-1 nevirapine resistant/CEMSS | 2.3 × 10$^{-8}$ | >10$^{-5}$ |
| HIV-1 IIIB/PBMC | <3 × 10$^{-11}$ | >10$^{-5}$ |
| HIV-2 D194/PBMC | >10$^{-5}$ | >10$^{-5}$ |
| HIV-1 IIIB/MT4 | <10$^{-12}$ | >10$^{-5}$ |
| HIV-1 4200 type E (primary isolate)/PBMC | <10$^{-10}$ | >10$^{-5}$ |
| HIV-1 6 type D (primary isolate)/PBMC | <10$^{-10}$ | >10$^{-5}$ |

TABLE 5

Inhibition of the inverse transcriptase of the HIV

| Compound | IC$_{50}$ (nM) |
|---|---|
| HEPT | >6000 |
| BPT | 400 |
| 7a | >10000 |
| 7c | 30 |
| 7e | >10000 |
| 8a | 100 |
| 8c | 15 |
| 8e | >4000 |
| 11b | >4000 |
| 11c | >4000 |
| 15 | 600 |
| 16 | 400 |

* HEPT = 1-[(2-hydroxyethoxymethyl]-6-(phenylthio)-thymine
** BPT = 1-benzyloxymethyl-6-(phenylthio)-thymine

TABLE 6

Activity of the isolated virions after treatment
with various inhibitors
The viral suspensions were tested at 100 TCID50.B The
results are compared with a viral supernatant having
been subjected to the same treatments and they
correspond to the mean of 1 to 4 experiments

| | | Concentration of the inhibitors | | |
|---|---|---|---|---|
| | | 10 μM | 1 μM | 0.1 μM |
| Nucleosidic analogues | AZT | 99% | 99% | — |
| | d4T | 127% | 130% | — |
| | ddl | 100% | 100% | — |
| | 3TC | 100% | 100% | — |
| Non-competitive inhibitors | HEPT | 141% | 121% | — |
| | TIBO | 155% | 155% | — |
| | Nevirapine | 111% | 86% | 86% |
| | Compound 7c | 0% | 1% | 60% |

TABLE 7

Inhibition of the endogenous IT by the
compound 7c ex vivo

| | IT activity in cpm | |
|---|---|---|
| Isolated virion | 813 | 809 |
| Compound 7c 10 μM | 32 | 852 |
| Compound 7c 100 μM | 32 | 222 |

We claim:

1. A compound of formula (3):

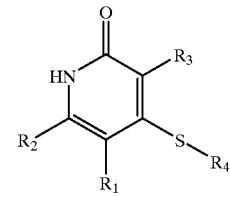

in which:

R$_1$ and R$_2$ independently represent an atom of hydrogen, an aliphatic group or an alkyloxyalkyl group in which the alkyl chains are from C$_1$ to C$_4$ or together form an aromatic ring;

R$_3$ represents:

an atom of hydrogen, or an NHR$_5$ group in which R$_5$ represents an atom of hydrogen or a COR$_6$ group in which R$_6$ is an aliphatic or aromatic group, or an NO$_2$ group or a COOR$_7$ group in which R$_7$ is an aliphatic group, R$_4$ represents a phenyl group.

2. The compound according to claim 1 wherein R$_1$ and R$_2$ independently represent an atom of hydrogen and an alkyl group from C$_1$ to C$_4$ or an alkyloxymethyl group.

3. The compound according to claim 1, wherein R$_3$ is an NH$_2$, NHCOCH$_3$, NO$_2$ or COOC$_2$H$_5$ group.

4. The compound according to claim 1, wherein $R_4$ is a phenyl group substituted with two methyl groups.

5. The compound according to claim 1, wherein two methyl groups are located in the meta positions of the phenyl group.

6. The compound according to claim 1, wherein said compound is 5-ethyl-6-methyl-3-carbethoxy-4-(3',5'-dimethylphenyl)thio-pyridin-2(1H)-one.

7. The compound according to claim 1, wherein said compound is 5-ethyl-6-methyl-3-nitro-4-(3',5'-dimethylphenyl)thio-pyridin-2(1H)-one.

8. The compound according to claim 1, wherein said compound is 3-amino-5-ethyl-6-methyl-4-(3',5'-dimethylphenyl)thio-pyridin-2(1H)-one.

9. The compound according to claim 1, wherein said compound is 3-amino-5-methyl-4-(3',5'-dimethylphenyl)thio-pyridin-2(1H)-one.

10. The compound according to claim 1, wherein said compound is 3-amino-5-ethyl-4-(3',5'-dimethylphenyl)thio-pyridin-2(1H)-one.

11. The compound according to claim 1, wherein said compound is 3-amino-5-ethoxymethyl-4-(3',5'-dimethylphenyl)thio-pyridin-2(1 H)-one.

12. The compound according to claim 1, wherein said compound is 5-ethyoxymethyl-3-nitro-4-(3',5'-dimethylphenyl)thio-pyridin-2(1H)-one.

13. A compound according to the following formula (6), in which $R_1$ and $R_2$ independently represent ethyl or methyl groups.

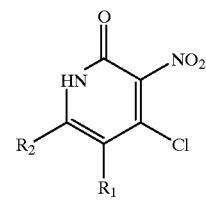

(6)

14. A compound according to the following formula (17), in which $R_1$ and $R_2$ independently represent ethyl or methyl groups.

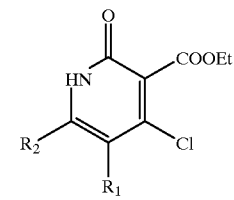

(17)

15. A pharmaceutical composition comprising an effective amount of the compound according to claim 1 in admixture with a pharmaceutically acceptable carrier.

16. A method for treatment of an illness linked to HIV, comprising the step of administering to a patient in need of said treatment an effective amount of a compound according to claim 1.

* * * * *